(12) United States Patent
Constantineau et al.

(10) Patent No.: US 10,569,017 B2
(45) Date of Patent: *Feb. 25, 2020

(54) PORTABLE DRUG MIXING AND DELIVERY DEVICE AND ASSOCIATED METHODS

(71) Applicant: Windgap Medical, Inc., Watertown, MA (US)

(72) Inventors: Cole Constantineau, Cambridge, MA (US); Christopher Stepanian, Somerville, MA (US); Adam Standley, Cambridge, MA (US); Brent Buchine, Austin, TX (US); Jeffrey Thomas Chagnon, Bow, NH (US); Michel Bruehwiler, Newton, MA (US)

(73) Assignee: Windgap Medical, Inc., Watertown, MA (US)

(*) Notice: Subject to any disclaimer, the term of this patent is extended or adjusted under 35 U.S.C. 154(b) by 31 days.

This patent is subject to a terminal disclaimer.

(21) Appl. No.: 15/873,073

(22) Filed: Jan. 17, 2018

(65) Prior Publication Data

US 2018/0140774 A1 May 24, 2018

Related U.S. Application Data

(63) Continuation of application No. 15/108,697, filed as application No. PCT/US2015/054611 on Oct. 8, (Continued)

(51) Int. Cl.
*A61M 5/19* (2006.01)
*A61M 5/20* (2006.01)
(Continued)

(52) U.S. Cl.
CPC ............ *A61M 5/19* (2013.01); *A61M 5/2033* (2013.01); *A61M 5/2066* (2013.01);
(Continued)

(58) Field of Classification Search
CPC ...... A61M 2005/202; A61M 2005/206; A61M 5/19; A61M 5/2033; A61M 5/2066; A61M 5/2448; A61M 5/2459; A61M 5/31596
See application file for complete search history.

(56) References Cited

U.S. PATENT DOCUMENTS 3,680,558 A 8/1972 Kapelowitz
3,946,732 A 3/1976 Hurscham
(Continued)

FOREIGN PATENT DOCUMENTS

EP 0961612 A1 12/1999
FR 2741810 B1 2/1998
(Continued)

*Primary Examiner* — Imani N Hayman
(74) *Attorney, Agent, or Firm* — Ascentage Patent Law, LLC; Travis Lee Johnson

(57) ABSTRACT

A telescoping portable drug mixing and delivery device configured to store a dry medication separately from a liquid component, wherein a tensile force applied between the housing and a cap opens a valve and causes displacement of a fluid from a first chamber to a second chamber while simultaneously mixing the fluid with a dry medicament prior to injection. An extendable needle guard is provided over the delivery assembly which prevents premature injection as well as inadvertent sticks or other cross contamination of a needle. The needle guard can also form part of a secondary trigger mechanism which injects the reconstituted drug after the mixing stage is complete.

20 Claims, 19 Drawing Sheets

Related U.S. Application Data 2015, now Pat. No. 9,907,910, and a continuation-in-part of application No. 14/255,909, filed on Apr. 17, 2014, now Pat. No. 10,195,361, which is a continuation of application No. 14/218,355, filed on Mar. 18, 2014, now Pat. No. 9,199,037.

(60) Provisional application No. 62/061,664, filed on Oct. 8, 2014, provisional application No. 61/917,943, filed on Dec. 19, 2013, provisional application No. 61/800,014, filed on Mar. 15, 2013.

(51) Int. Cl.
*A61M 5/315* (2006.01)
*A61M 5/24* (2006.01)

(52) U.S. Cl.
CPC ........ *A61M 5/2448* (2013.01); *A61M 5/2459* (2013.01); *A61M 5/31596* (2013.01); *A61M 2005/202* (2013.01); *A61M 2005/206* (2013.01)

(56) References Cited

U.S. PATENT DOCUMENTS

| | | | |
|---|---|---|---|
| 4,031,892 A | 6/1977 | Hurschman |
| 4,060,082 A | 11/1977 | Lindberg et al. |
| 4,529,403 A | 7/1985 | Kamstra |
| 4,643,721 A | 2/1987 | Brunet |
| 4,755,169 A | 7/1988 | Sarnoff et al. |
| 5,360,410 A | 11/1994 | Wacks |
| 5,569,193 A | 10/1996 | Hofstetter et al. |
| 5,704,918 A | 1/1998 | Higashikawa |
| 5,899,881 A | 5/1999 | Grimard et al. |
| 6,149,628 A | 11/2000 | Szapiro et al. |
| 6,309,372 B1 | 10/2001 | Fischer et al. |
| 6,641,561 B1 | 11/2003 | Hill et al. |
| 6,656,150 B2 | 12/2003 | Hill et al. |
| 6,770,052 B2 | 8/2004 | Hill et al. |
| 6,793,646 B1 | 9/2004 | Giambattista et al. |
| 6,852,103 B2 | 2/2005 | Fowles et al. |
| 6,953,445 B2 | 10/2005 | Wilmot et al. |
| 7,449,012 B2 | 11/2008 | Young et al. |
| 7,544,189 B2 | 6/2009 | Griffiths |
| 7,556,614 B2 | 7/2009 | Griffiths et al. |
| 7,608,055 B2 | 10/2009 | Griffiths et al. |
| 7,621,887 B2 | 11/2009 | Griffiths et al. |
| 7,678,073 B2 | 3/2010 | Griffiths et al. |
| 7,749,190 B2 | 7/2010 | Griffiths et al. |
| 7,757,370 B2 | 7/2010 | Griffiths |
| 7,776,015 B2 | 8/2010 | Sadowski et al. |
| 7,947,742 B2 | 5/2011 | Batycky et al. |
| 8,057,427 B2 | 11/2011 | Griffiths et al. |
| 8,092,420 B2 | 1/2012 | Bendek et al. |
| 8,123,719 B2 | 2/2012 | Edwards et al. |
| 8,177,758 B2 | 5/2012 | Brooks et al. |
| 8,187,220 B2 | 5/2012 | Griffiths et al. |
| 8,251,947 B2 | 8/2012 | Kramer et al. |
| 8,496,619 B2 | 7/2013 | Kramer et al. |
| 8,506,526 B2 | 8/2013 | Griffiths et al. |
| 8,568,367 B2 | 10/2013 | Griffiths et al. |
| 8,613,720 B2 | 12/2013 | Bendek et al. |
| 8,632,504 B2 | 1/2014 | Young |
| RE44,847 E | 4/2014 | Sadowski et al. |
| 8,696,618 B2 | 4/2014 | Kramer et al. |
| 8,784,372 B1 | 7/2014 | Hoggatt |
| 8,814,834 B2 | 8/2014 | Sund et al. |
| 8,870,827 B2 | 10/2014 | Young et al. |
| 8,945,053 B2 | 2/2015 | Vogt et al. |
| 9,364,610 B2 | 6/2016 | Kramer et al. |
| 9,364,611 B2 | 6/2016 | Kramer et al. |
| 2002/0042592 A1 | 4/2002 | Wilmot et al. |
| 2002/0046563 A1 | 4/2002 | Wakui et al. |
| 2002/0049406 A1 | 4/2002 | Hill et al. |
| 2002/0049407 A1 | 4/2002 | Hill et al. |
| 2005/0074498 A1 | 4/2005 | Tarara et al. |
| 2005/0148933 A1 | 7/2005 | Raven et al. |
| 2005/0177100 A1 | 8/2005 | Harper et al. |
| 2006/0079834 A1 | 4/2006 | Tennican et al. |
| 2007/0116729 A1 | 5/2007 | Palepu |
| 2007/0202163 A1 | 8/2007 | Rawas-Qalaji et al. |
| 2007/0293582 A1 | 12/2007 | Hill |
| 2008/0103490 A1 | 5/2008 | Edwards et al. |
| 2008/0281271 A1 | 11/2008 | Griffiths et al. |
| 2009/0171311 A1 | 7/2009 | Genosar et al. |
| 2010/0228190 A1 | 9/2010 | Griffiths et al. |
| 2010/0318035 A1 | 12/2010 | Edwards et al. |
| 2011/0092906 A1 | 4/2011 | Böttger et al. |
| 2011/0092917 A1 | 4/2011 | Wei et al. |
| 2011/0237681 A1 | 9/2011 | Batycky et al. |
| 2012/0016296 A1 | 1/2012 | Charles |
| 2012/0130318 A1 | 5/2012 | Young |
| 2012/0179137 A1 | 7/2012 | Rush et al. |
| 2012/0302989 A1 | 11/2012 | Kramer et al. |
| 2013/0018310 A1 | 1/2013 | Boyd et al. |
| 2013/0018313 A1 | 1/2013 | Kramer et al. |
| 2013/0023822 A1 | 1/2013 | Edwards et al. |
| 2013/0060232 A1 | 3/2013 | Adlon et al. |
| 2013/0178823 A1 | 7/2013 | Buchine et al. |
| 2013/0274707 A1 | 10/2013 | Wilmot et al. |
| 2013/0289791 A1 | 10/2013 | Kerrigan et al. |
| 2013/0317477 A1 | 11/2013 | Edwards et al. |
| 2013/0331788 A1 | 12/2013 | Kramer et al. |
| 2014/0088512 A1 | 3/2014 | Quinn |
| 2014/0276385 A1 | 9/2014 | Buchine et al. |
| 2014/0276430 A1 | 9/2014 | Baker et al. |
| 2014/0336589 A1 | 11/2014 | Sund et al. |
| 2015/0011975 A1 | 1/2015 | Anderson et al. |
| 2015/0174323 A1 | 6/2015 | Edwards et al. |
| 2015/0367073 A1 | 12/2015 | Standley et al. |
| 2015/0374925 A1 | 12/2015 | Standley et al. |
| 2016/0220764 A1 | 8/2016 | Durvasula et al. |

FOREIGN PATENT DOCUMENTS

| | | |
|---|---|---|
| WO | 9208506 A1 | 5/1992 |
| WO | 2005032523 A1 | 4/2005 |
| WO | 2008114035 A1 | 9/2008 |
| WO | 2008154092 A1 | 12/2008 |
| WO | 2009118754 A3 | 12/2009 |
| WO | 2010022870 A1 | 3/2010 |
| WO | 2010068415 A1 | 6/2010 |
| WO | 2011060541 A1 | 5/2011 |
| WO | 2011109340 A1 | 9/2011 |
| WO | 2012090168 A1 | 7/2012 |
| WO | 2012099898 A2 | 7/2012 |
| WO | 2013063707 A1 | 5/2013 |
| WO | 2014026694 A1 | 2/2014 |
| WO | 2014066731 A1 | 5/2014 |
| WO | 2014080020 A1 | 5/2014 |
| WO | 2014060563 A3 | 7/2014 |
| WO | 2014195183 A1 | 12/2014 |
| WO | 2014205463 A1 | 12/2014 |
| WO | 2015071289 A1 | 5/2015 |

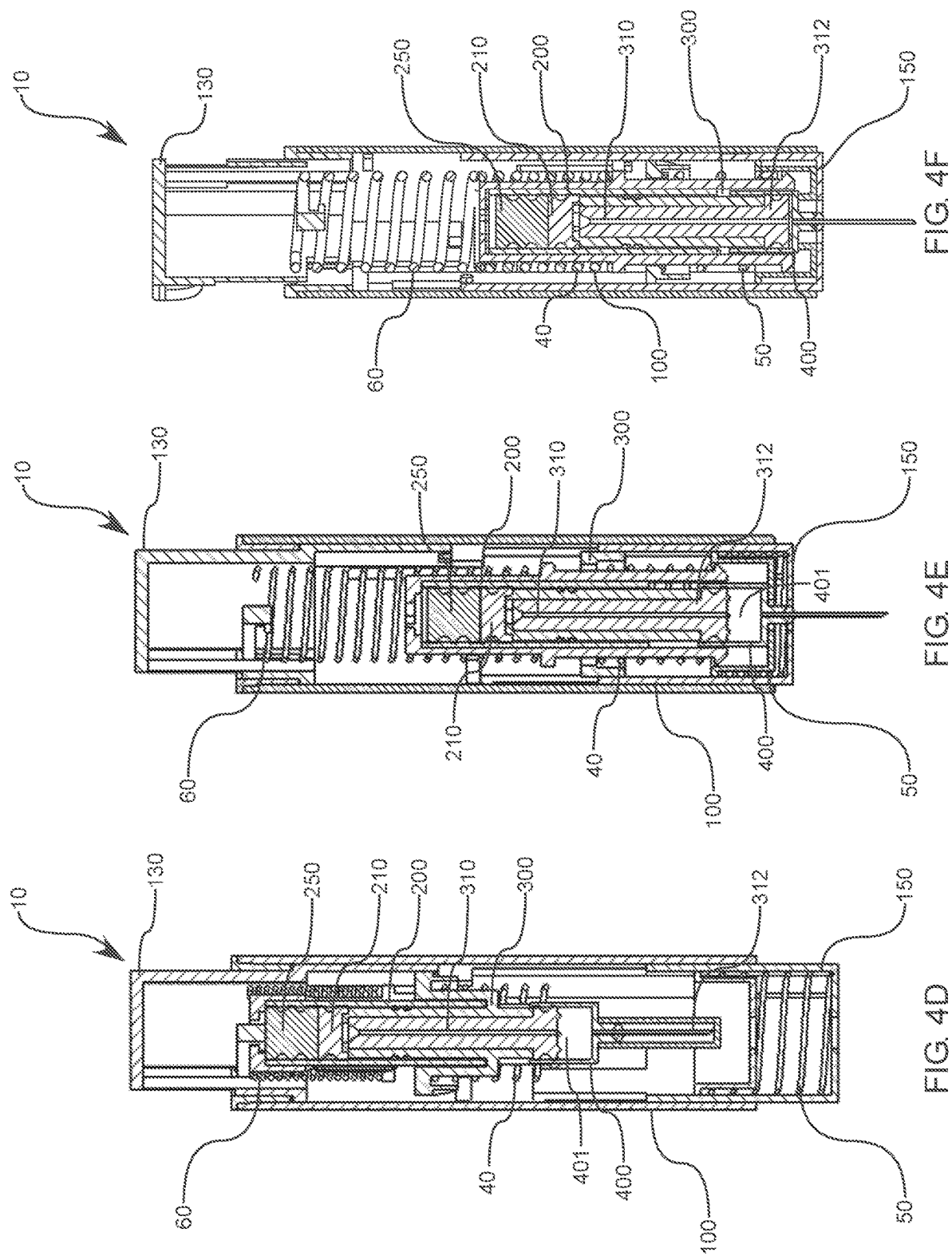

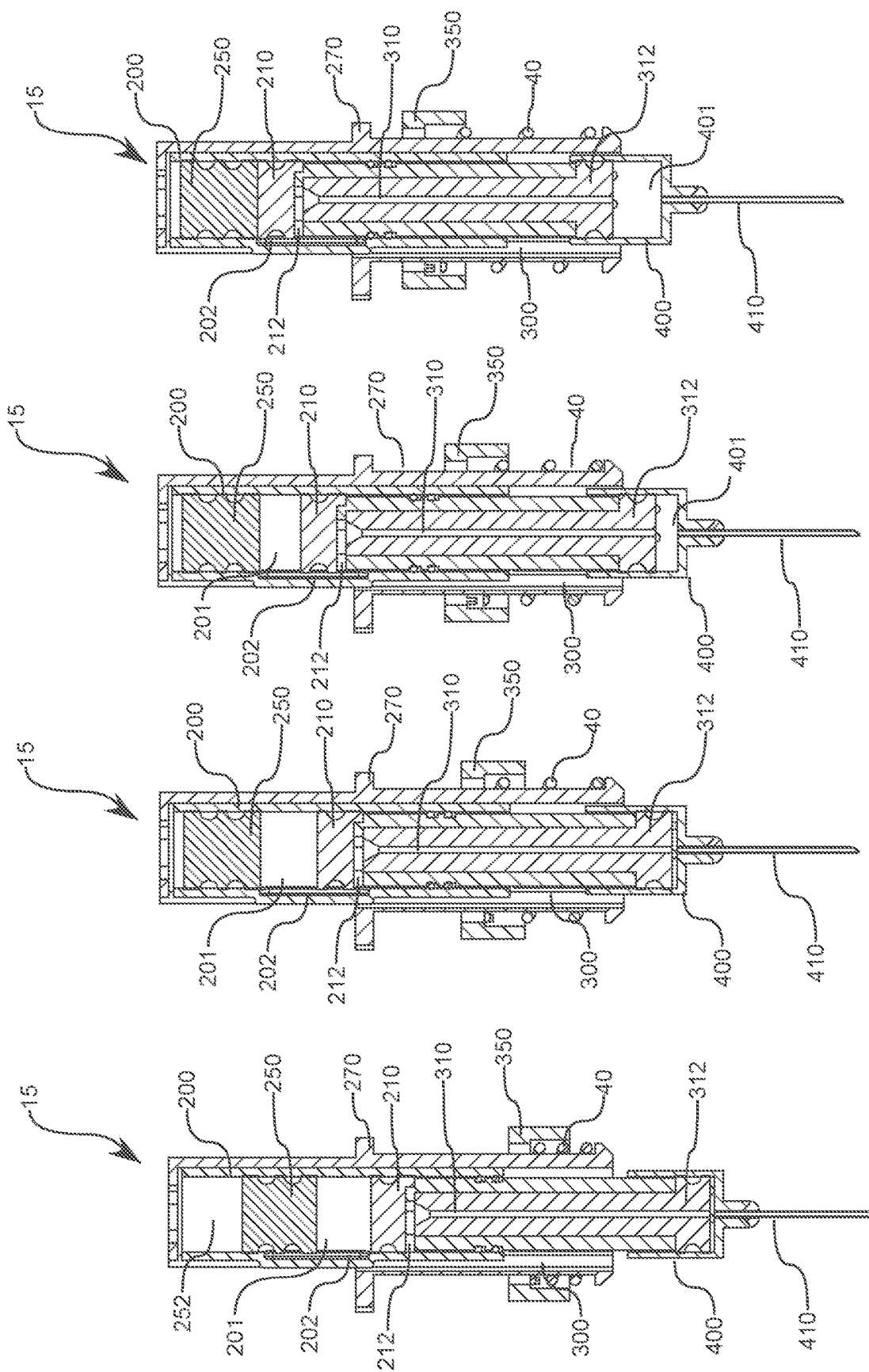

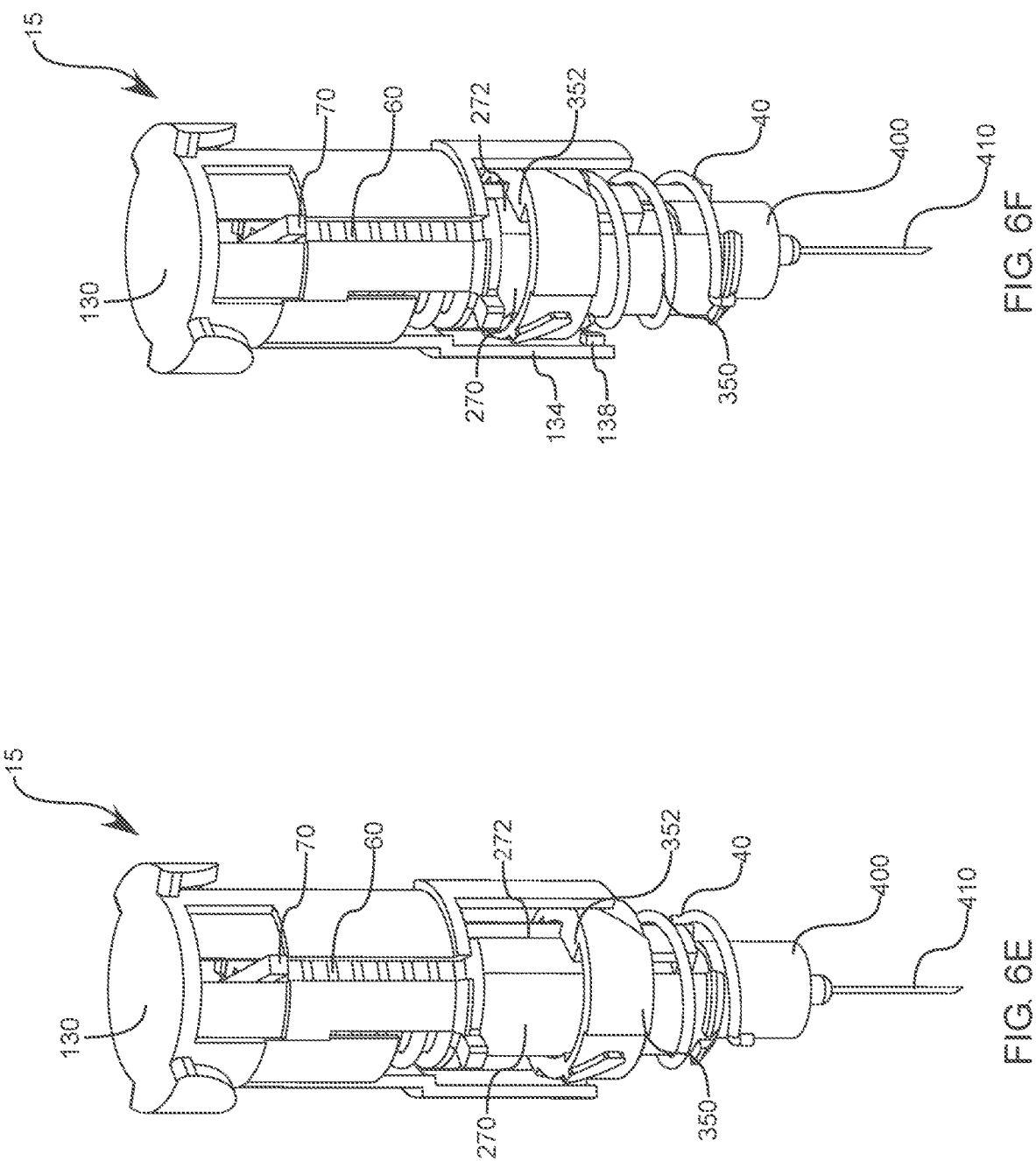

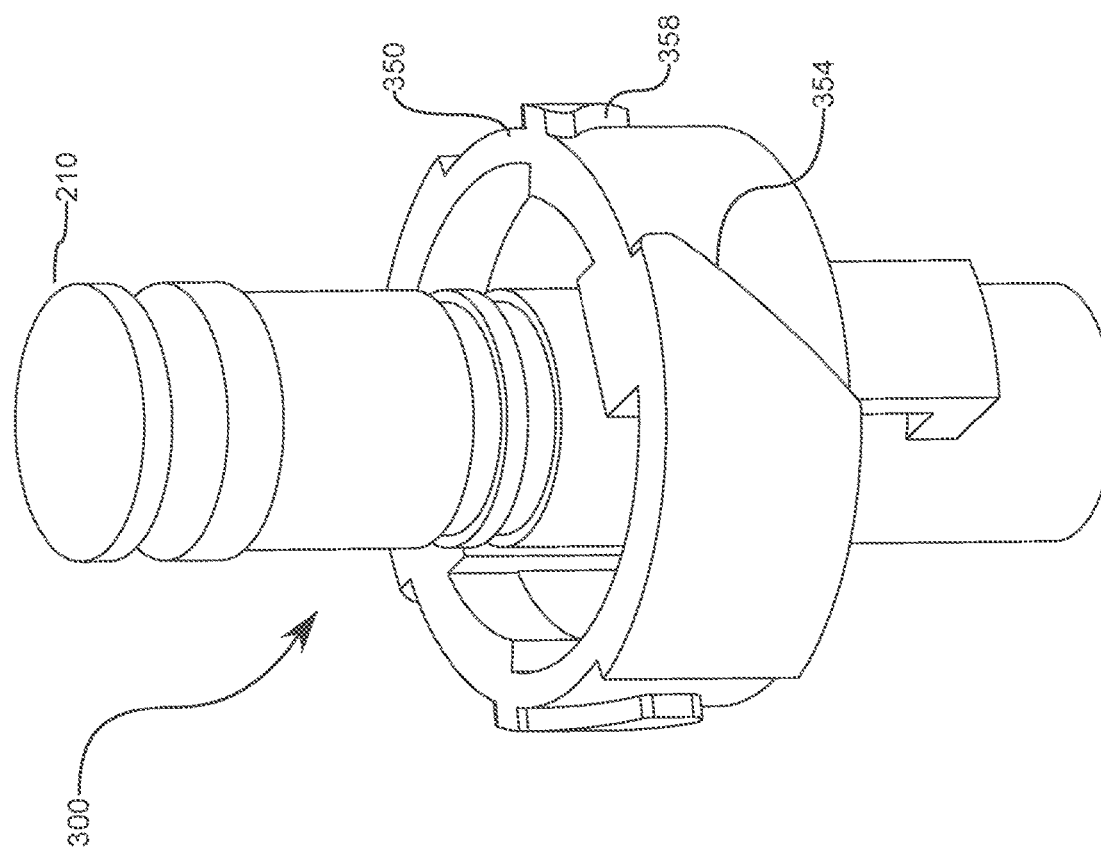
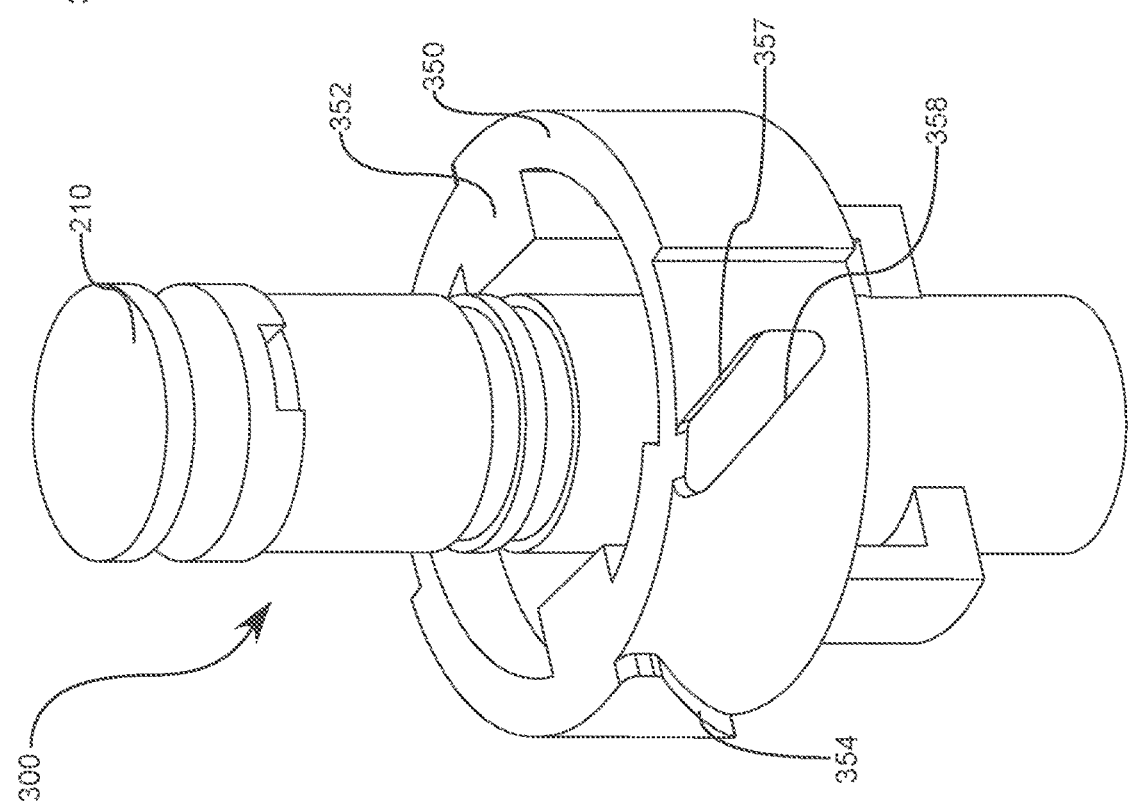

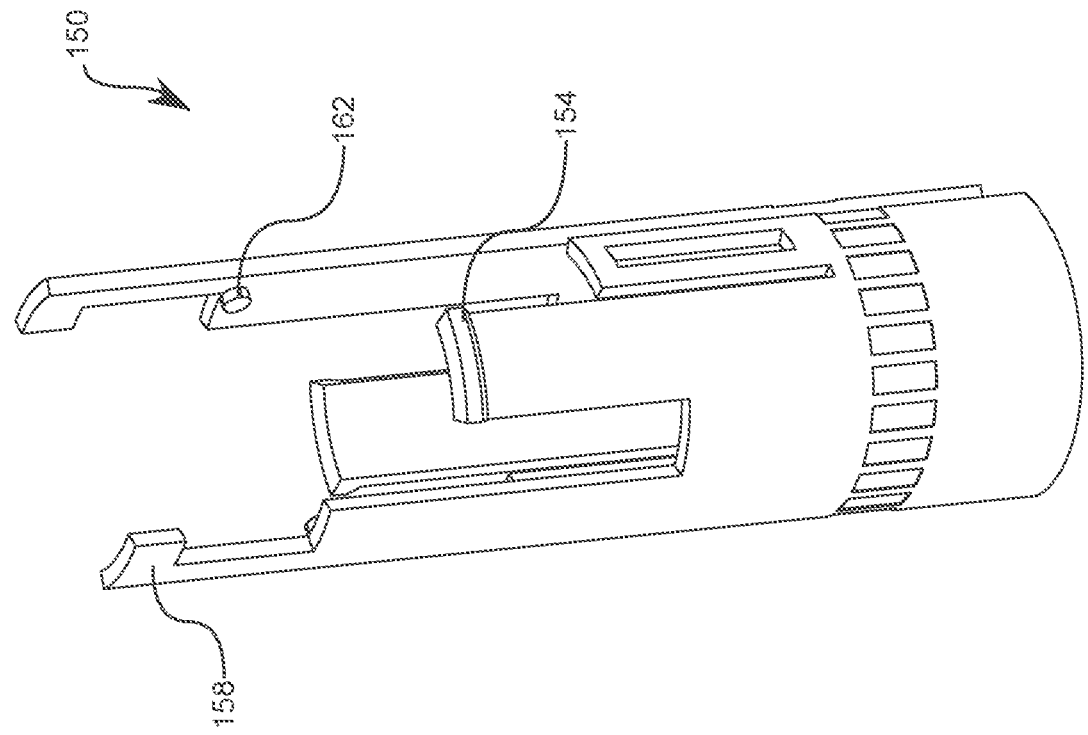
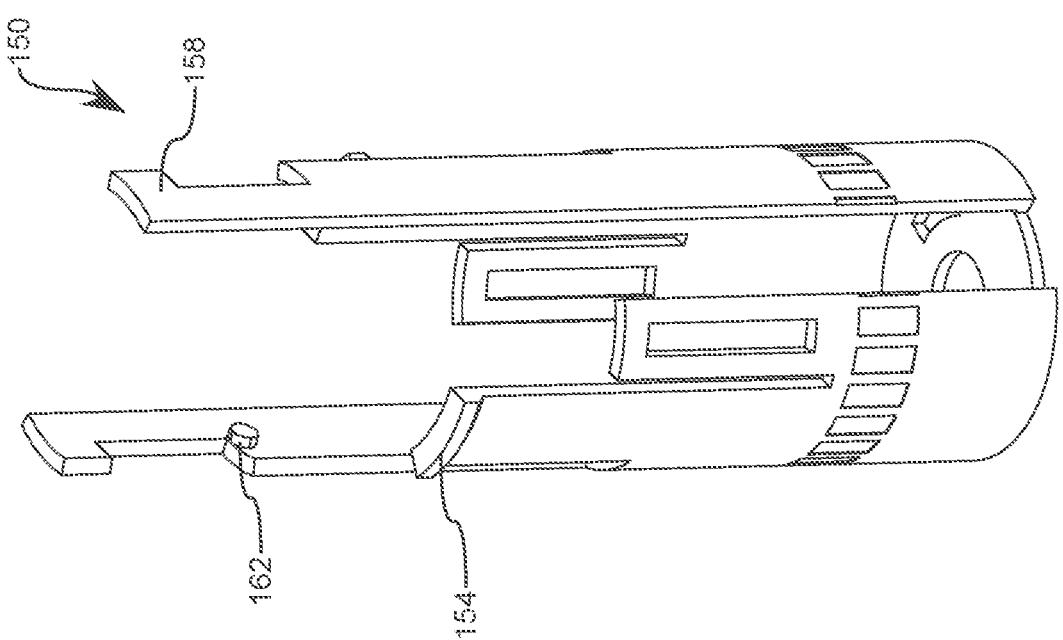

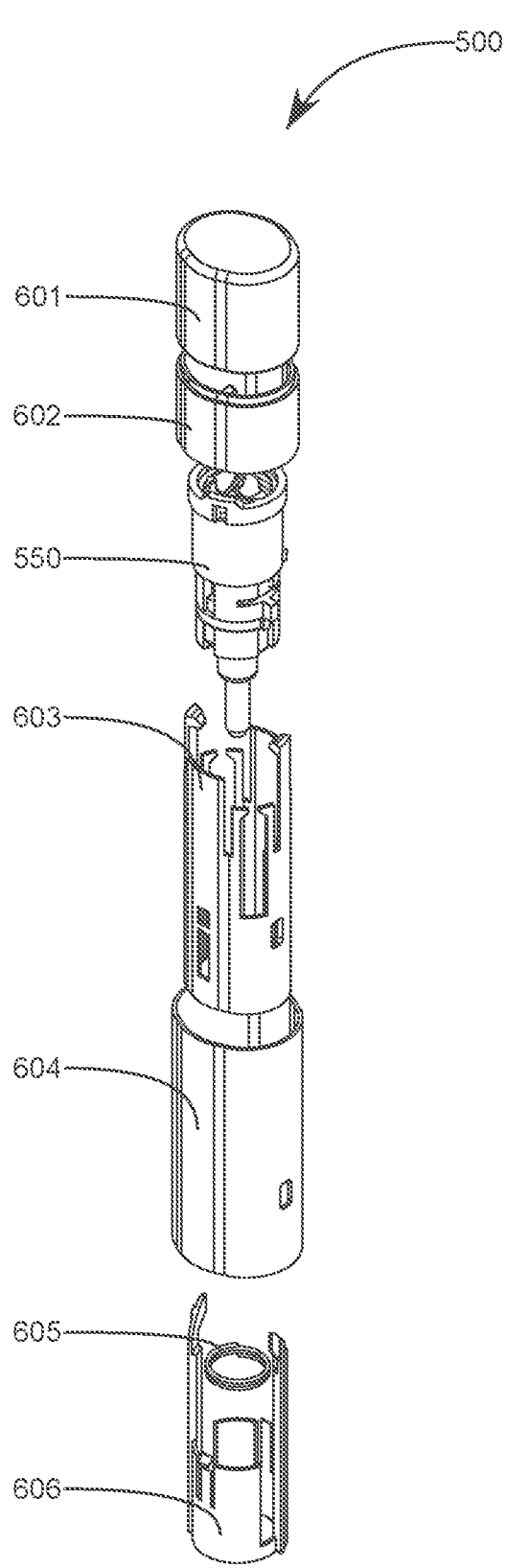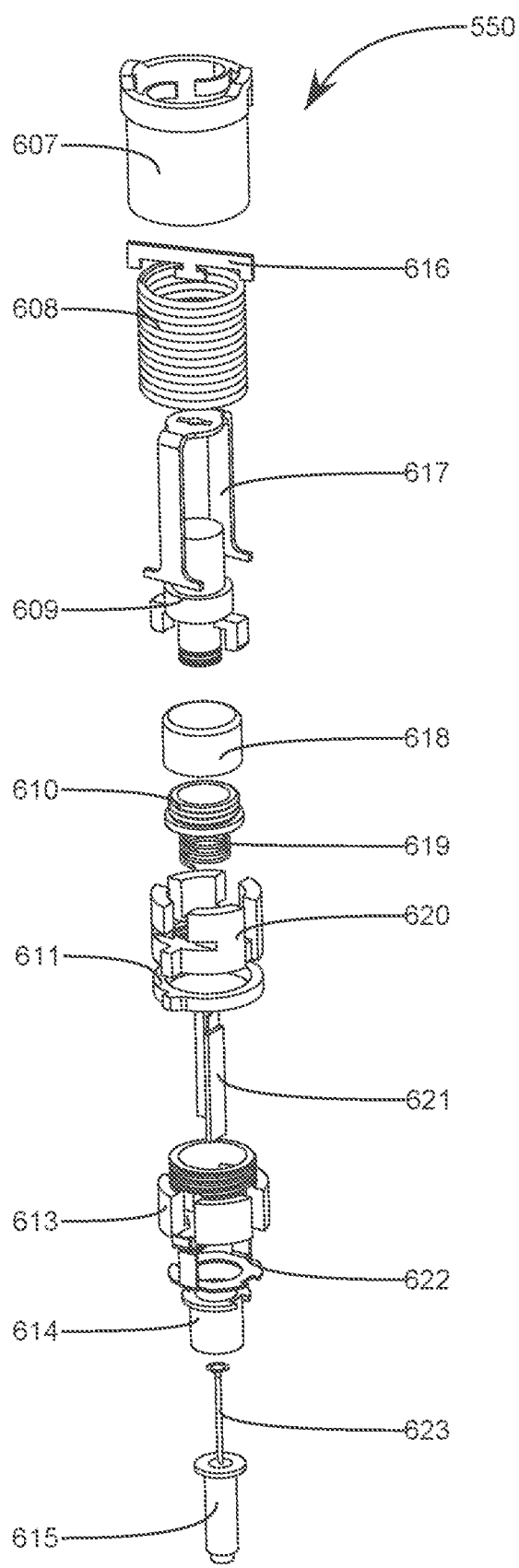
FIG. 12A
FIG. 12B

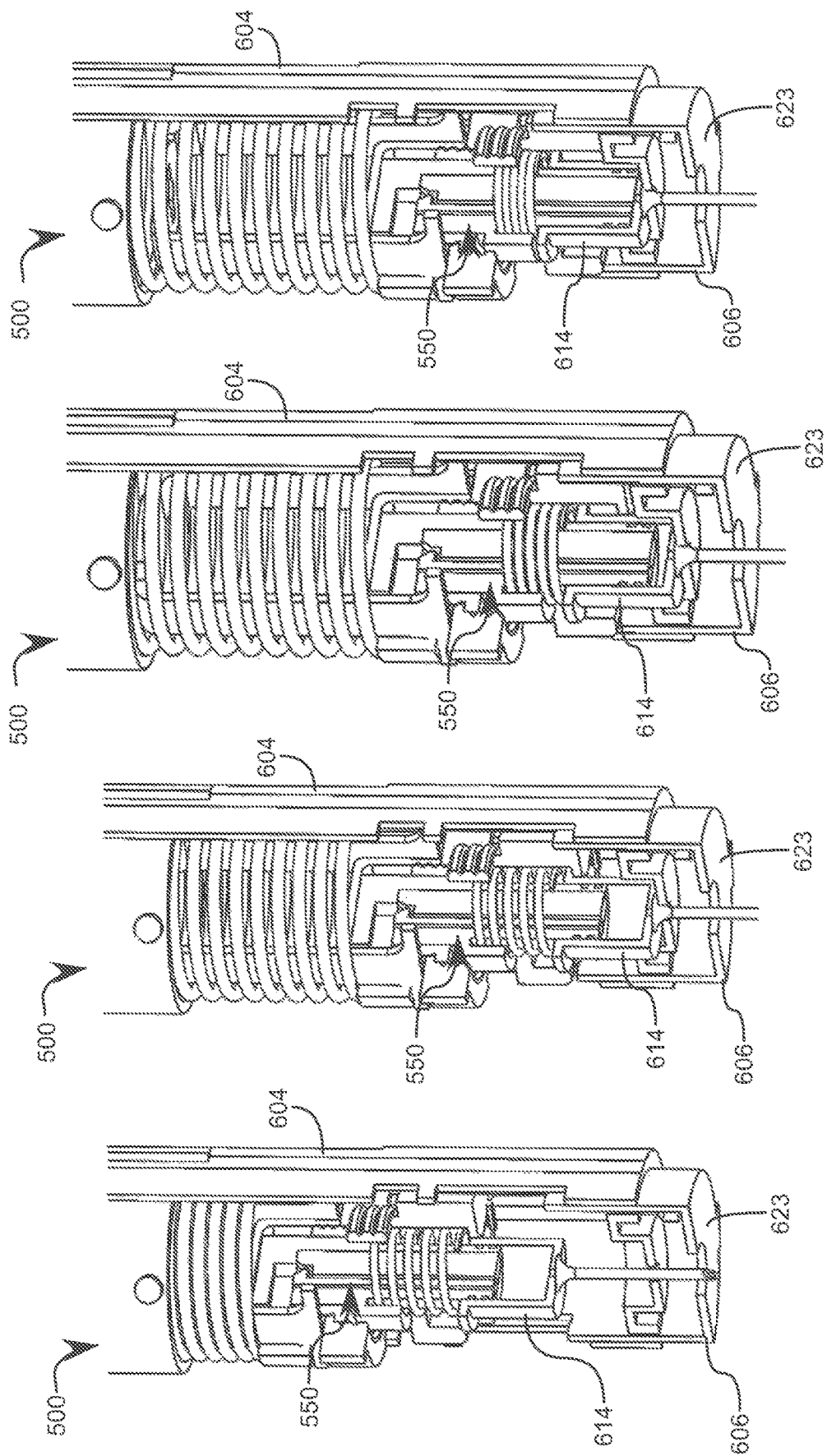

PORTABLE DRUG MIXING AND DELIVERY DEVICE AND ASSOCIATED METHODS

CROSS-REFERENCE TO RELATED APPLICATIONS

This application claims the benefit of each of the following co-pending applications: U.S. patent application Ser. No. 15/108,697 filed on Aug. 1, 2018, and all priority claimed applications claimed therefrom, which are all herein incorporated by reference in their entirety.

FIELD OF THE INVENTION

The present invention relates generally to auto-injectors and prefilled syringes and more particularly to auto-injectors that store in a compact state and allow for formation or reconstitution of a therapeutic agent for injection.

BACKGROUND OF THE INVENTION

Individuals who suffer from certain medical conditions are often required to keep an auto-injector or prefilled syringe nearby in order to address a medical need. A few examples of this are insulin pens for people with diabetes, epinephrine for those with food and insect stings allergies, and antidotes for soldiers at risk of exposure to chemical and/or biological toxins in the field. For example, an allergic reaction may occur in a location which is physically distant from the nearest hospital or medical facility. For example, bee stings, are more likely to occur outside than indoors. Food containing peanuts are more likely to be supplied to the individual away from a controlled home environment like at a baseball park. Having a portable epinephrine auto-injector nearby enables emergency intervention after an exposure to an allergen.

Size is an issue when it comes to auto-injectors. Many owners of the devices are hesitant to carry their injector with them if it represents a burden, by providing injectors in more compact sizes it will make it more likely that they will.

Shelf-life is also a large issue with respect to auto-injectors, which can be expensive and used fairly infrequently. For example, a user who has intense allergic reactions to shellfish can go years between exposures and subsequent injections. In such a case it can be easy to forget to replace the auto-injector after expiration, whereupon in an emergency, the drugs contained therein have expired and are either ineffective or have a greatly reduced effectiveness due to decomposition of the drugs contained therein. As will be appreciated by those having skill in the art, the shelf life can be increased by storing the desired medication in an unmixed and dry state and dissolved just prior to injection. This ability to store the wet and dry components separately within the device can increase the shelf life and thus increase the likelihood that the user will have an injector with effective dosages when an emergency arises.

In such devices it is required that the mixing and reconstitution processes are consistent and complete prior to injection.

SUMMARY OF THE INVENTION

It has been recognized that if a drug can be kept out of the liquid phase and stored as a dry medication, the shelf-life can be increased substantially while temperature susceptibility can be decreased substantially, thus allowing the efficacy and potency of the drug to endure longer and through harsher environments.

It has been recognized that a smaller drug delivery device than a conventional epinephrine auto-injector, which could be attached to a key chain and/or easily fit in a person's pocket, would make the device easier to carry and more likely that the user will have it on their person when needed. Various structures are contemplated herein, which address many of the problems discussed above through the use of mixing structures, and actuation devices, which ensure proper storage integrity, and full mixing prior to injection.

Contemplated herein is a medication mixing and delivery device, A medication mixing and delivery device which includes a housing which contains a first chamber, a second chamber, and a compression chamber located within the housing, wherein each chamber has a selectively changeable effective volume. A fluidic channel can be provided and disposed between the first and second chambers as well as a seal which can be positioned between the first chamber and the compression chamber. In addition, a movable body can be provided which is disposed between the first and second chamber.

A mixing actuation device can then be coupled to the movable body, wherein activation of the mixing actuation device facilitates the selective reduction of the effective volume of the first chamber, the selective reduction of the effective volume of the compression chamber, and displacement of a liquid stored in the first chamber from the first chamber into the second chamber via the fluidic channel.

Further, a delivery assembly can be provided in fluid communication with the second chamber and which facilitates delivery to the user, such as through a needle to an injection site.

In some embodiments a dry medicament can be provided within the housing and outside the first chamber such as in the fluidic channel or within the second chamber.

In yet additional embodiments the drug mixing and delivery device can include a fluidic bypass formed in a sidewall of the first chamber. In some such embodiments the fluidic channel can be provided through the movable body and is selectively placed into fluidic communication with the fluidic bypass upon translation of a mixing displacement mechanism, i.e. a plunger which can be affixed to the movable body.

In yet additional embodiments the seal can be provided as a dynamic seal which is configured to flex or translate axially.

In yet other embodiments a mixing displacement device can be coupled to the movable body, wherein the mixing actuation device is activated through application of an axial tensile force, which axial tensile force releases a stop and allows the movable body and mixing displacement mechanism to translate in a first direction.

In yet additional embodiments an intermediate stopping mechanism can be provided wherein the intermediate stopping mechanism prevents fluid communication from the second chamber to the delivery assembly prior to activating a delivery actuation device.

In some of the embodiments shown herein the drug mixing and delivery device of can further include two independent and directionally opposing springs, wherein one spring is a mixing spring that is coupled to the mixing actuation device and upon triggering the mixing actuation device releases energy from the mixing spring that directs the movable body in a first direction, and wherein the other spring is a delivery spring that is coupled to a delivery actuation device and upon triggering the delivery actuation device releases energy that directs the movable body in a second direction.

In yet additional embodiments the medication mixing and delivery device can also include a needle shield assembly, the needle shield assembly having a needle shield and a needle shield spring, the needle shield spring biasing the needle shield in an extended position. In some such embodiments the needle shield forms a part of the delivery actuation device, the delivery actuation device being configured to displace the movable body downward so as to displace the fluid out of the second chamber through the delivery assembly, and whereupon depressing the needle shield toward the housing triggers actuation of the delivery actuation device.

In additional embodiments the needle shield assembly further includes a locking mechanism, which is triggered after a first needle shield depression, and wherein the locking mechanism is configured to lock the needle shield in an extended position after being removed from an injection site.

In yet additional embodiments an additional delivery actuation device can be provided which is also coupled to a delivery spring that, upon activating, the delivery actuation device causes energy from the delivery spring to be released and cause the movable body, which is coupled to a delivery displacement mechanism, to translate in an opposite direction of the movement initially facilitated by the mixing actuation device, thus facilitating displacement of liquid transferred to the second chamber from the first chamber to be displaced through the delivery assembly.

In some embodiments the compression chamber can contain a gas and the chamber is configured to vent the gas upon activating the mixing actuation device, wherein the volume of gas contained therein is displaced in part by the dynamic seal.

In yet additional embodiments the mixing and delivery device can include a delivery actuation device, and wherein the mixing actuation device and the delivery actuation device are each coupled to a multi-cam system. In some such embodiments the multi-cam system can include a plurality of camming features, ramps, etc.

In yet additional embodiments the medication mixing and delivery device can include a mixing spring coupled to the mixing actuation device, wherein the mixing spring is initially stored in torsion and compression, and whereupon activating the mixing actuation device releases the torsional force and an extension force of the spring. In some such embodiments the mixing spring can be re-torqued prior to activating the delivery actuation device, wherein the torque released is directed to and rotates the movable body about an axis.

In yet other embodiments a method for mixing and delivering a medication is contemplated wherein the steps of the method can include: activating a mixing actuation device of a medication mixing and delivery device that translates a movable body, wherein the medication mixing and delivery device includes: a housing; a first chamber, a second chamber and a compression chamber located within the housing, wherein each chamber has a selectively changeable effective volume; a fluidic channel disposed between the first and second chambers; a seal positioned between the first chamber and the compression chamber; the movable body disposed between the first and second chamber, the movable body being coupled to a mixing displacement mechanism; the mixing actuation device coupled to the movable body; and a delivery assembly configured to be in fluid communication with the second chamber; displacing the effective volume of the compression chamber by causing the mixing displacement mechanism coupled to the movable body to translate toward the dynamic seal; displacing a liquid stored in the first chamber through the fluidic channel into the second chamber; and displacing the liquid now stowed in the second chamber through the delivery device.

In additional embodiments the method can further include the step of releasing a torsional and compression force stored in a mixing spring that is coupled to the mixing actuation device, wherein the compression force from the mixing spring provides energy for the movable body to translate toward the seal, wherein the released torsional force acts on and causes the movable body to rotate about an axis.

In additional embodiments the method can further include the step of arming a delivery actuation device upon activation of the first actuation device by re-torqueing the mixing spring prior to displacing the liquid now stowed in the second chamber.

In additional embodiments the method can further include the step of activating the delivery actuation device that is coupled to a delivery spring, whereupon activation of the delivery actuation device releases energy stored in the delivery spring and causes the movable body, which is coupled to delivery displacement device, to translate towards the second chamber and displace a liquid that was previously displaced from the first chamber through the delivery assembly.

In additional embodiments the method can further include the step of mixing the liquid with a dry medicament stored in the housing outside of the first chamber prior to displacing the now mixed liquid through the delivery assembly.

In additional embodiments the method can further include the step of activating the mixing actuation device step by pulling an extension trigger that releases a stop thereby allowing energy stored in a mixing spring to be released.

In additional embodiments the step of displacing an effective volume from the compression results in either a gas stored in the compression chamber to be compressed or vented out through a vent.

In yet additional embodiments a medication mixing and delivery device is contemplated which includes a housing; a compression chamber located within the housing and having a dynamic seal about one end; a first chamber located within the housing proximal a first end, wherein the first chamber further includes: an effective volume defined between a first displacement mechanism and the dynamic seal, the first displacement mechanism being configured to selectively reduce the effective volume of the first chamber; a fluidic bypass provided in a sidewall being configured to selectively bypass the first displacement mechanism; a second chamber located within the housing configured to receive a volume of liquid being displaced from the first chamber by the first displacement mechanism, the second chamber having an effective volume defined between a second displacement mechanism and an opposing wall; a movable body disposed between the first and second chamber, the movable body further being coupled to the first and second displacement mechanism; a mixing actuation device coupled to the movable body, wherein activation of the mixing actuation device displaces the movable body in a first direction which displacement causes the first displacement mechanism to reduce the effective volume of the first chamber; a delivery assembly configured to be in fluid communication with the second chamber; and a delivery actuation device coupled to a second trigger, wherein activation of the delivery actuation device displaces the movable body in a second direction which displacement causes the second displacement mechanism to reduce the effective volume of the second chamber.

The second direction some instances is opposite of that of the first direction and in other instances it is in a direction that is different than the first direction.

In some such embodiments the mixing actuation device can be activated through application of an axial tensile force, which axial tensile force is configured to release a first stop of the mixing actuation device and allows the movable body and first displacement mechanism to displace in the first direction, establish fluidic communication between the first and second chambers, and thus displace a liquid component from the first chamber, through at least the fluidic bypass, and into the second chamber.

In yet additional embodiments a medication mixing and delivery device is contemplated which includes: a housing having a chamber, wherein a medicament is stored therein; a needle shield assembly that is coupled to a first actuation device, wherein the needle shield assembly is comprised of a needle shield and a pre-stored energy source, wherein the needle shield is initially positioned in a stowed state prior to activating the first actuation device, which first actuation device causes a first portion of the needle shield to extend indicating a ready state; a second actuation device coupled to the needle shield assembly, wherein the extended first portion functions as a trigger for the second actuation device and upon depressing the first portion activates the second actuation device; and a delivery assembly configured to be in fluid communication with the chamber.

In some such embodiments activating the delivery actuation device can cause or establish fluidic communication between the chamber and the delivery mechanism, and further releases a locking mechanism that releases energy stored in the pre-stored energy source that directs the needle shield to extend to a position beyond that of the delivery assembly.

In yet additional embodiments a medication mixing and delivery device is contemplated which includes: a housing; a first chamber and a second chamber located within the housing, wherein each chamber has a selectively changeable effective volume; a fluidic channel disposed between the first and second chambers; a movable body disposed between the first and second chamber; a mixing actuation assembly coupled to the movable body and a mixing spring, wherein activation of the actuation device facilitates the rotation and translation of the movable body about an axis, the selective reduction of the effective volume of the first chamber, and a transferring of liquid stored in the first chamber to be displaced from the first chamber and enter into the second chamber via the fluidic channel. This embodiment can further include a delivery assembly configured to be in fluid communication with the second chamber.

In some such embodiments the medication mixing and delivery device can further include a torqueing component configured to cause torsion in the mixing spring during the actuation of the mixing actuation assembly.

In some such embodiments the medication mixing and delivery device can further include a compression chamber separated from the first chamber by a dynamic seal.

In some such embodiments the medication mixing and delivery device can further include a delivery actuation assembly configured to transfer fluid from the second chamber through the delivery assembly.

In some such embodiments the delivery actuation can be coupled to an extendable trigger, whereupon triggering the extendable trigger causes the delivery actuation assembly to actuate wherein the mixing actuation assembly is coupled to the extendable trigger, and causes a portion of the extendable trigger to be extended during actuation of the mixing actuation assembly and wherein triggering the extendable trigger causes the mixing spring to release a torsional force.

In some such embodiments depressing of the extendable trigger can cause energy from a pre-loaded needle assembly energy source to be released that extends a portion of the needle shield assembly to extend beyond the delivery assembly. In some such embodiments a locking mechanism can be provided that prevents the extended needle shield assembly from retracting after being extended beyond the delivery assembly.

In some additional embodiments, the medication mixing and delivery device can further include a torqueing component in the form of a multi-cam system.

In yet additional embodiments a method for mixing and delivering a medication, the method is contemplated which involves various steps, such steps including: releasing energy stored in a pre-torqued and pre-compressed mixing spring, wherein the release of energy causes a movable body, disposed between a first and second chamber disposed in the housing of a mixing device, to rotate and translate about an axis; displacing an effective volume of the first chamber with a displacement device coupled to the movable body; transferring a fluid stored in the first chamber through a fluidic channel to the second chamber; re-torqueing the mixing spring; releasing energy from the re-torqued spring that causes the movable body to rotate again; transferring fluid from a second chamber through a delivery assembly.

This method can further include providing a delivery system coupled to the mixing device, wherein the delivery system includes a delivery actuation assembly coupled to the movable body.

This method can further include extending a trigger coupled to the delivery actuation assembly; activating a trigger coupled to the delivery actuation assembly; and depressing the trigger, whereby energy is released from a delivery spring that causes the delivery actuation device to translate the movable body.

In yet additional embodiments a medication mixing and delivery device is contemplated which includes: a housing having a first chamber and a second chamber with selectively variable effective volumes; a first and second displacement component mechanically coupled to a multi-cam system; a pre-loaded energy source coupled to the multi-cam system; a first and second trigger coupled to the multi-cam system, wherein triggering the first trigger causes energy to be released from the pre-stored energy and direct the first displacement component to displace a liquid stored in the first chamber through a fluidic channel into the second chamber, and wherein triggering the second trigger releases additional energy that directs the second displacement component to displace liquid now stored in the second chamber to be displaced and exit through a delivery assembly that is in fluid communication with the second chamber.

In some such devices the multi-cam system can include a three-cam component. Additionally some such devices a mixing spring and a delivery spring which function as pre-loaded energy sources for driving the various steps or moving into the various states.

In yet additional embodiments the medication and delivery device can further include a movable body disposed between the first and second chambers, wherein the movable body is coupled to the multi-cam system and is configured to rotate and translate about an axis.

In yet additional embodiments the medication and delivery device a needle shield assembly can be incorporated into the second trigger, wherein the multi-cam system allows the second trigger to partially extend upon release of energy from the pre-loaded energy source. In some such embodiments the needle shield of the needle shield assembly can be configured to extend beyond the delivery assembly upon depressing the second trigger.

In yet another embodiment a medication and delivery device comprises a housing having a first chamber and a second chamber with selectively variable effective volumes; a first and second displacement component coupled to a single actuation assembly that is coupled to a first and second spring, wherein actuating the actuation assembly a first time releases energy stored in the first spring that drives the first displacement component in a first direction, and wherein actuating the actuation assembly a second time releases energy stored in the second spring that drives the second displacement component in a second direction that is different that the first direction, wherein the first actuation causes liquid to transfer from the first chamber to the second chamber, and wherein the second actuation causes fluid to transfer from the second chamber through a delivery assembly.

Alternative methods can include various manufacturing and assembly steps for a mixing and delivering device, such methods including various steps such as: providing a needle shield; extending the needle shield in response to the mixing actuation, wherein a subsequent depression of the needle shield causes initiates the delivery actuation.

These aspects of the invention are not meant to be exclusive and other features, aspects, and advantages of the present invention will be readily apparent to those of ordinary skill in the art when read in conjunction with the following description, appended claims, and accompanying drawings. Further, it will be appreciated that any of the various features, structures, steps, or other aspects discussed herein are for purposes of illustration only, any of which can be applied in any combination with any such features as discussed in alternative embodiments, as appropriate.

BRIEF DESCRIPTION OF THE DRAWINGS

The foregoing and other objects, features, and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention, wherein:

FIGS. 4A-F illustrate various cross-sectional views of a portable drug mixing and delivery device in accordance with the embodiments of either FIGS. 1A-E or FIGS. 2A-E;

FIGS. 5A-D illustrate a mixing assembly for use in either of the portable drug mixing and delivery devices illustrated in FIGS. 1A-E or FIGS. 2A-E;

FIGS. 6A-F illustrate various stages of a mixing mechanism and process which is applicable to either of the portable drug mixing and delivery devices illustrated in FIGS. 1A-E or FIGS. 2A-E;

FIGS. 8A-B illustrate various front and side views of a movable body and an associated cam ring mechanism for use in either of the portable drug mixing and delivery devices illustrated in FIGS. 1A-E or FIGS. 2A-E;

FIGS. 9A-B illustrate various perspective and cross-sectional views of a needle shield for use in either of the portable drug mixing and delivery devices illustrated in FIGS. 1A-E or FIGS. 2A-E;

FIGS. 12A-B illustrate exploded perspective views of yet another embodiment of a portable drug mixing and delivery device in accordance with various aspects of the present invention as well as a mixing assembly for use therein;

FIGS. 16A-D illustrate partial side cut away views of the portable drug mixing and delivery device of embodiment of FIGS. 12A-B which illustrate various injection actuation steps which further illustrate various aspects of the present invention.

DETAILED DESCRIPTION OF THE INVENTION

It will be appreciated by those having skill in the area of fabrication and storage of drugs, that the lifespan and effectiveness of the drug can be increased substantially by keeping the medication in a dry state. Storage in a dry state also decreases the rate of degeneration as well as the degenerative effects of temperature, for example heat exposure. By keeping the drug in a dry state, the breadth of environments where the device can be stored is increased while decreasing the frequency of required replacement.

The present invention illustrates various principles and devices which allow for the storage of a device having two or more components contained therein but which can quickly and reliably reconstitute, dissolve, fluidize, and/or put into a suspension, the components, i.e. mix them, immediately prior to delivery.

As such, a system and method for storing and/or mixing a dry medicament component with a wet component for delivery to a user is contemplated herein.

Figure 1E:
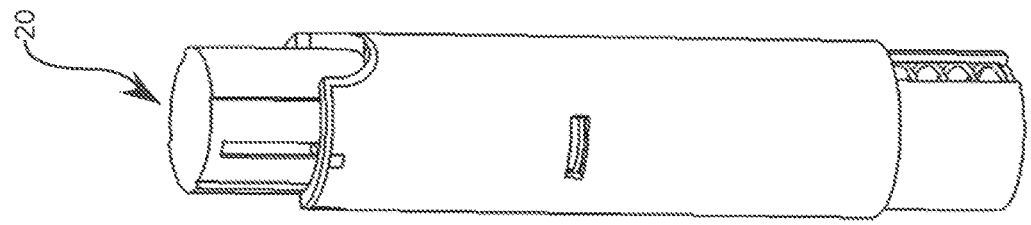
FIGS. 1A-E illustrate a portable drug mixing and delivery device in accordance with various aspects of the present invention.
Figure 1D:
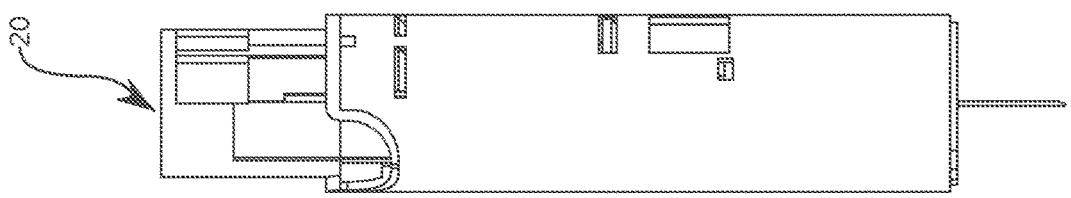
Figure 1C:
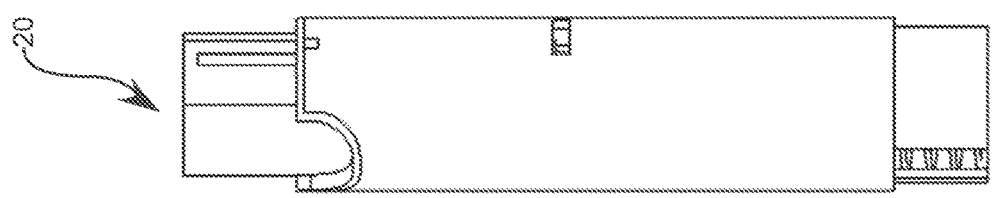
Figure 1B:
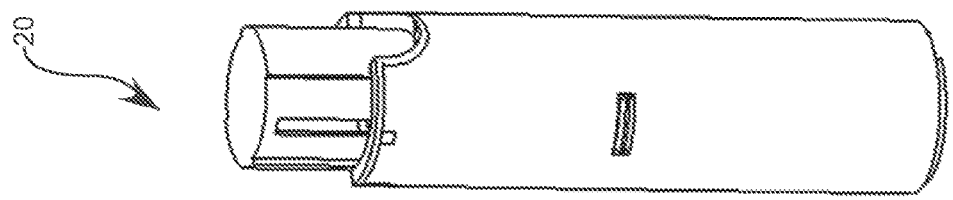
Figure 1A:
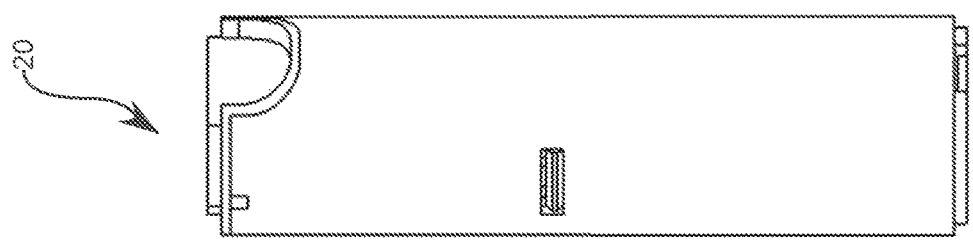
Figure 2E:
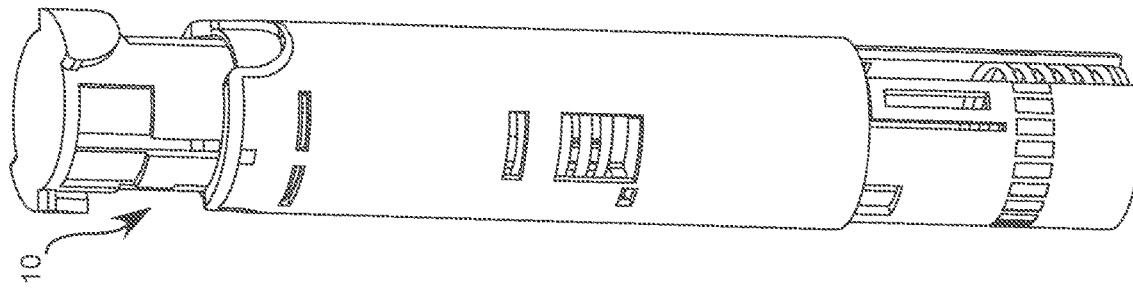
FIGS. 2A-E illustrate another portable drug mixing and delivery device in accordance with additional aspects of the present invention.
Figure 2D:
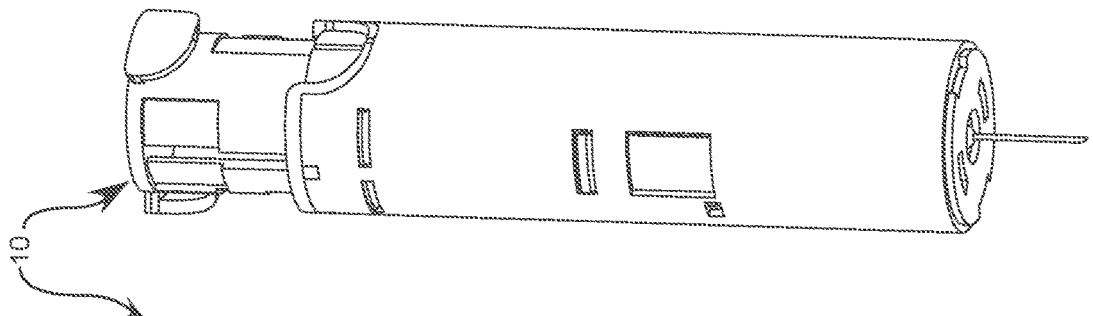
Figure 2C:
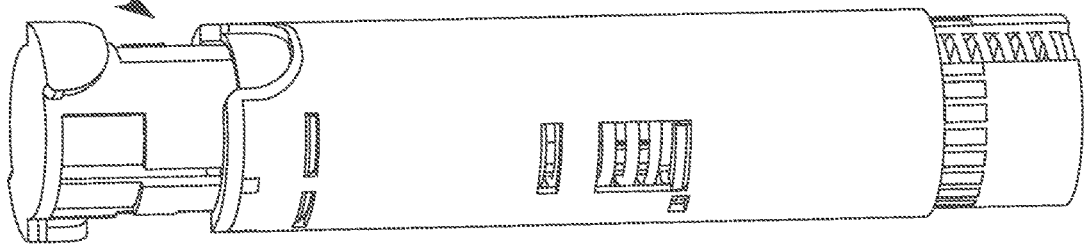
Figure 2B:
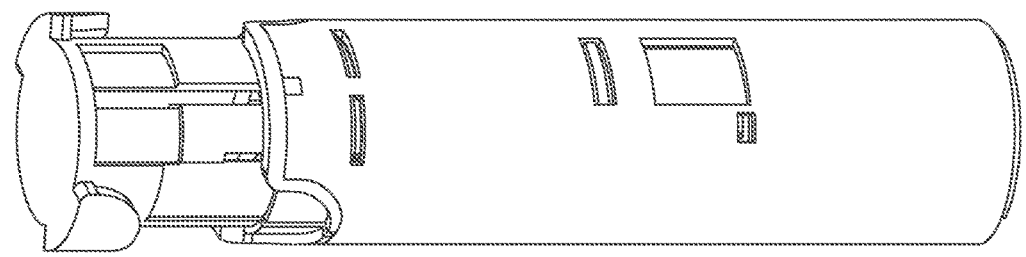
Figure 2A:
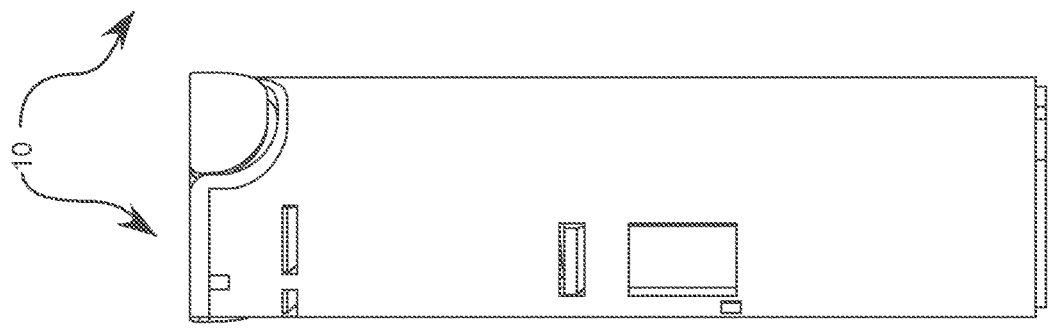

As illustrated in FIGS. 1A-E and FIGS. 2A-E. The system can include an auto-injector, 10 and 20, which illustrate a stowed state in FIGS. 1A and 2A. The auto injector, 10 or 20, is activated by pulling or extending the device, which extension initiates and actuates a first mixing step, as shown in FIGS. 1B and 2B. Once mixing is complete, a needle shield is released and permitted to extend, as shown in FIGS. 1C and 2C, wherein a subsequent re-depression of the needle shield operates as a trigger for an injection step which operates to eject the needle and inject the mixed drug to an injection site, as shown in FIGS. 1D and 2D.

As the auto injector device is pulled away from the injection site the needle shield is automatically extended and locked into the extended state, blocking the needle, so as to minimize the visibility of the needle pre and post injection, and thus prevent accidental sticks to the user or others in the vicinity. A locking mechanism can thus be provided so as to lock the needle shield in the extended position. In one embodiment the extended arms of the needle shield can be caused to interfere with corresponding protrusions within the housing, or alternatively the needle shield can be provided with radially outward biased tabs which lock into a corresponding slot in the housing.

Figure 3:
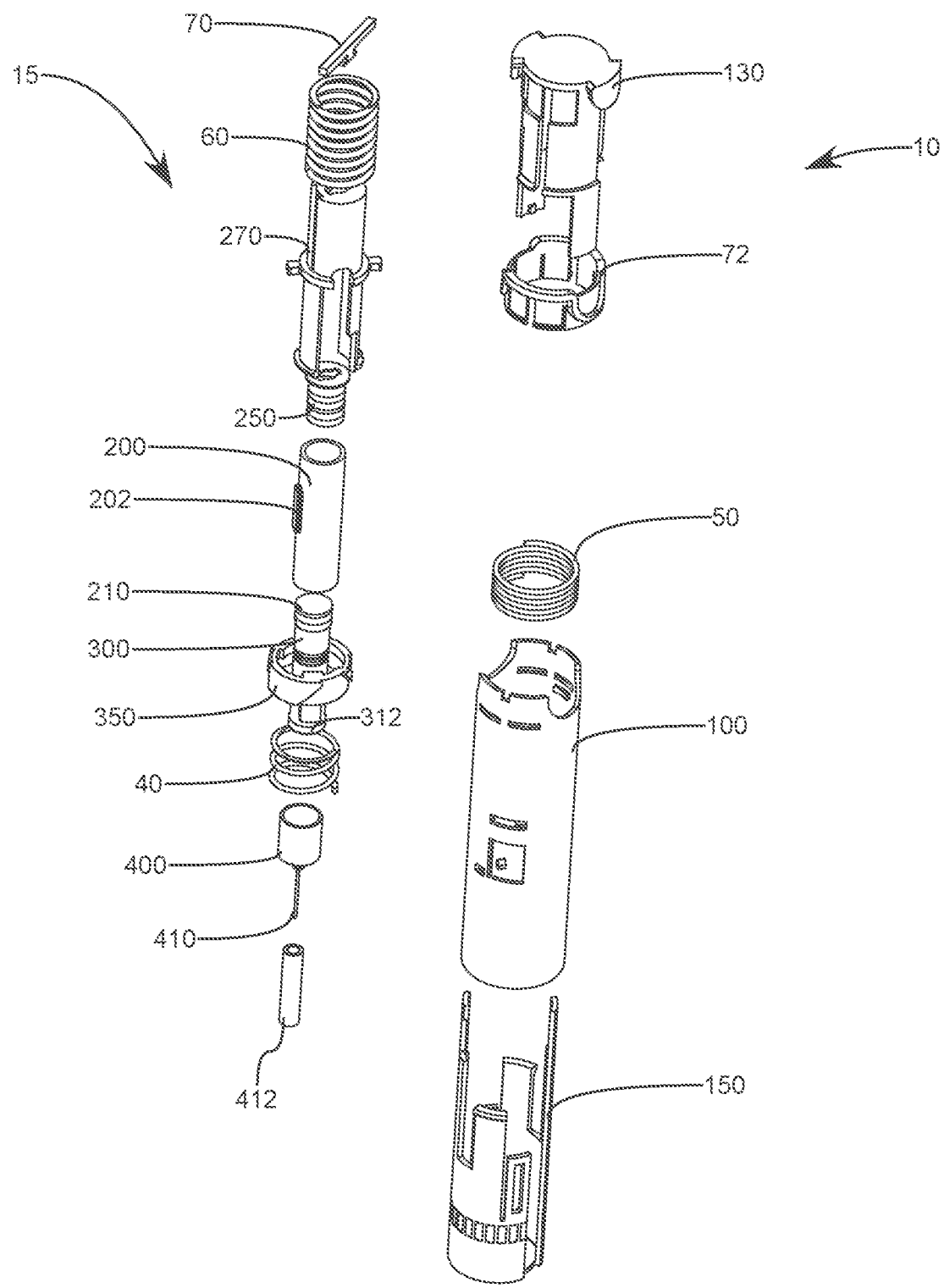
FIG. 3 illustrates an exploded view of the portable drug mixing and delivery devices illustrated in FIGS. 2A-E.

With reference to FIG. 3, shown is an exploded view of an auto injector assembly 10 and internal mixing assembly 15, which illustrates the various individual components and will be helpful in explaining the interplay between the various components below.

The auto injector assembly 10 can include an external housing 100. A needle shield 150 can have a needle shield spring 50 which can be biased so as to extend the needle shield 150 axially with respect to the housing 100 in a downward or injection direction. The upper end of the housing can be provided with a hanger retention clip 72 and a telescoping component 130, wherein the telescoping component 130 can be pulled and extended with respect to the housing 100 so as to initiate and actuate a mixing step, which mixing step will be discussed in more detail below.

The mixing assembly 15 can include a plurality of vials 200 and 400 with a movable body 300 disposed there between. The movable body 300 can have an actuation device in the form of a cam ring 350 disposed thereon, wherein the cam ring 350 facilitates movement of plungers 210 and 312 into the first and second vials 200 and 400 respectively during mixing and subsequent injection steps. A mixing spring 40 can facilitate axial and rotational motion of certain steps of the cam ring 350 and an injection spring 60 can facilitate downward axial displacement of the entire mixing assembly 15 during an injection step which can cause an injection assembly to extend, i.e. the needle 410 to pierce the membrane 412, wherein the mixed drug can then be ejected through the needle 410 and into an injection site. The injection assembly 15 can further include a dynamic seal 250 and a vial sleeve 270 and a hanger 70 that will be discussed in greater detail below as they relate to the mixing and injection steps. Additionally, the vial 200 can be provided with a fluidic bypass 202 which structure and functionality will be discussed in more detail below.

With reference to FIGS. 4A-F and FIGS. 5A-D shown is an exemplary embodiment of an auto-injector 10 and a mixing assembly 15 contained therein in accordance with various aspects of the present invention embodiment which illustrates various states through the actuation of the auto-injector from a stowed to an injected state.

The auto-injector 10 can include a housing 100 which houses a plurality of vials 200 and 400, which can form first and second chambers 201 and 401 respectively. The first chamber 201 can be defined as a space between a first plunger 210 and a dynamic seal 250 within the first vial 200. This first chamber 201 can be configured to initially hold a first component of an unmixed medicament. The second chamber 401 can be defined as a space between a second plunger 312 and a bottom and side-walls of the second vial 400. This second chamber 401 can be configured to initially hold a second component of an unmixed medicament. A fluidic channel 310 can be provided between the first and second chambers through a movable body 300, which separates the two chambers. The fluidic channel 310 can provide selective fluidic communication between the first and second chambers by means of axially translating the movable body 300 with respect to the first vial 200, which will be discussed in more detail below.

Figure 4A:
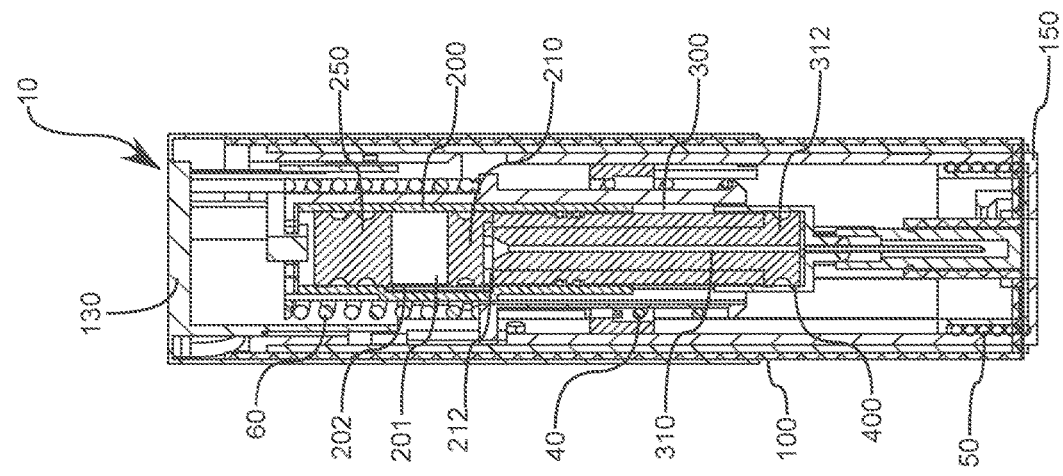
Figure 4B:
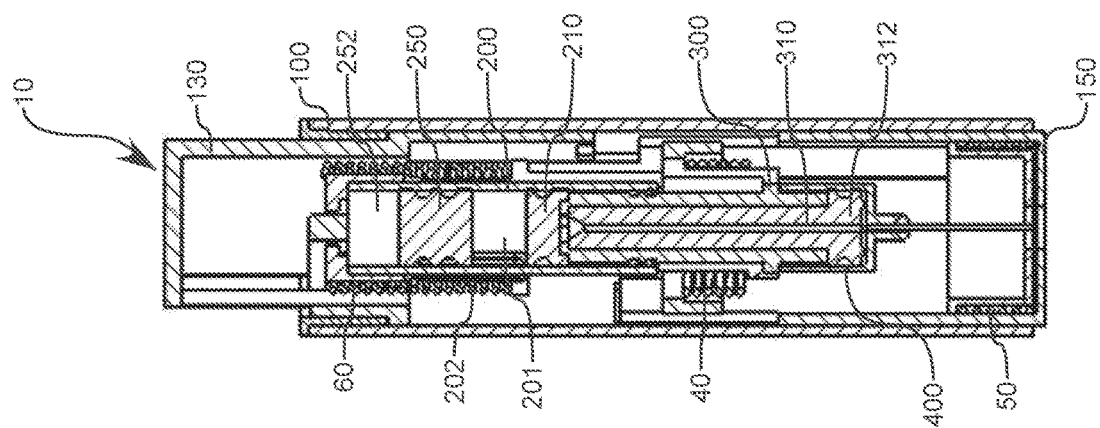
Figure 4C:
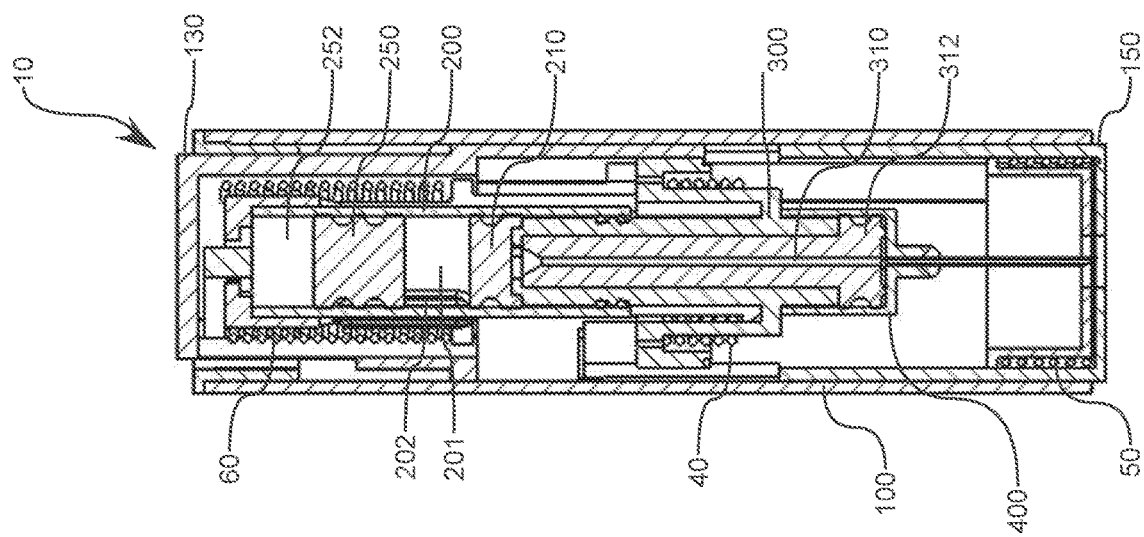

In order to initiate change from a stowed state, as shown in FIG. 4A, to a mixed state, as shown in FIG. 4D, a telescoping component 130 can be extended with respect to the housing 100, the extension causing a portion of the telescoping component 130 to interact with various actuating mechanisms of the movable body 300 causing it to translate axially with respect to the first vial, establish fluidic communication between the first and second chambers, and move the first plunger 210 thus reducing the effective volume of the first chamber and displacing the first component through the fluidic channel 310 and into the second chamber 401. This displacement can cause the first component of the medicament to mix with the second component of the medicament, i.e. a dry medicament, which second component can be stored within the fluidic channel 310 or within the second vial 400 itself.

In the embodiments shown the dry medicament can be contained within a second chamber 401 or within a fluidic channel 310 which connects the two chambers, or within a recess formed at an opening or outlet thereof. The orientation of this embodiment includes a movable body 300 which pushes a first plunger 210 or other displacement mechanism upwards into the first chamber 201.

It will be appreciated that, with respect to gasses, most fluids are considered incompressible. In order to facilitate upward motion of the first plunger 210 or displacement mechanism, and the fluid contained within the first chamber 201, a third plunger or dynamic seal 250 and a compression chamber 252 can be provided wherein a compressible gas is provided within the compression chamber 252 or the gas contained therein is permitted to exit the compression chamber 252 freely. In some embodiments, as shown, the dynamic seal 250 can be provided as a movable plunger. In yet additional embodiments the dynamic seal can be provided as a flexible membrane that is allowed to stretch, deform, or otherwise conform in response to an increase in pressure in the first chamber 201, so as to allow upward translation of the first displacement mechanism or plunger 210.

The upward translation of the first plunger 210 creates a pressure on the incompressible fluid of the first medicament component which presses on the dynamic seal 250 or secondary movable wall, causing the dynamic seal to translate upward and allowing both the dynamic seal and the first plunger 210 to each translate upward in the direction of the compression chamber 252 until a plunger channel 212 aligns with a fluidic bypass channel 202 formed in a sidewall of the first vial 200. Once the plunger channel 212 is aligned, fluidic communication is established between the first chamber 201 and the second chamber 401 and the fluid or first medicament component is permitted to be displaced through the plunger channel 212, through the fluidic channel 310, and into the second chamber 401 as the first plunger 210, or other displacement mechanism, reduces the effective volume of the first chamber 201. It will be appreciated that the fluidic bypass channel 202 is sufficient in length in an axial direction such that it can circumvent the first plunger 210 along then entire length of upward travel of the first plunger 210 within the first vial 200 until the effective volume of the first chamber is reduced to near zero by the first plunger being displaced upward by the movable body 300. In the embodiment shown, the plunger channel 212 can be provided as a radially disposed slot on its bottom surface so as to allow fluid to travel from the bypass channel 202 which is located about the perimeter of the first vial 200, to the inlet of the fluidic channel 310, which is located about a central portion of the movable body and into the second chamber 401.

In the embodiment shown, as the movable body is displaced upward, and mixing is achieved through the displacement of the movable body in an upward axial direction with respect to the housing, which can be facilitated by a mixing spring 40, the upward motion of the movable body 300 can effectuate the release of a stop, which will be discussed in more detail below, which interferes with the extension of the needle shield 150. In this manner, the needle shield 150 can be extended and serve as a secondary trigger for triggering the device to move from the mixed state to injected state. In the embodiments shown, the needle shield 150 can be provided with a needle shield spring 50 which can effectuate such extension and arming of the second trigger step.

Figure 6D:
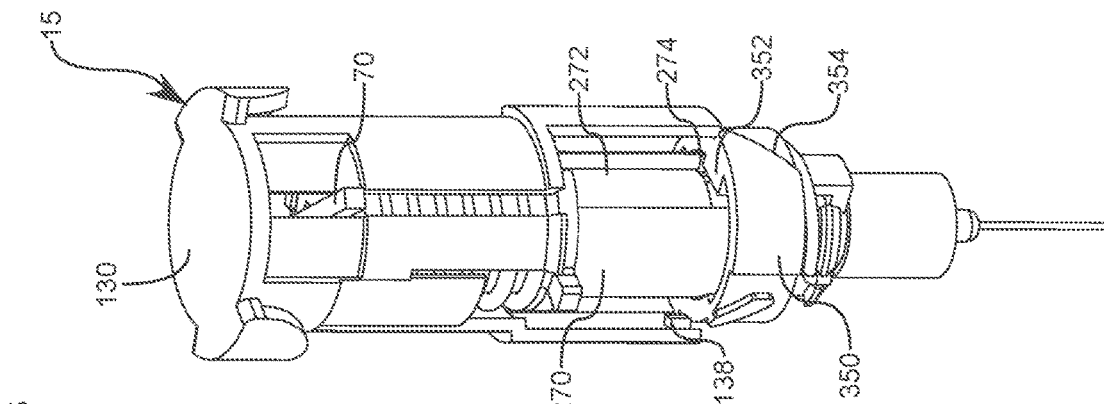
Figure 6C:
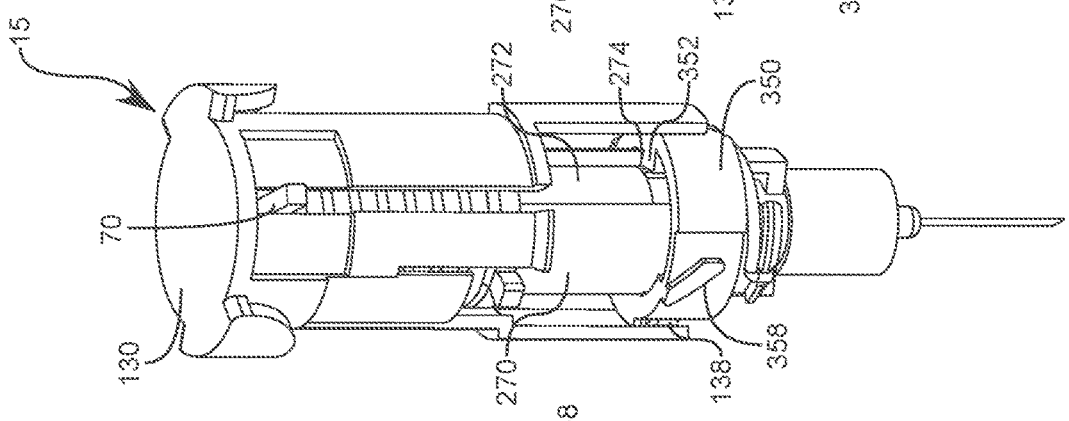
Figure 6B:
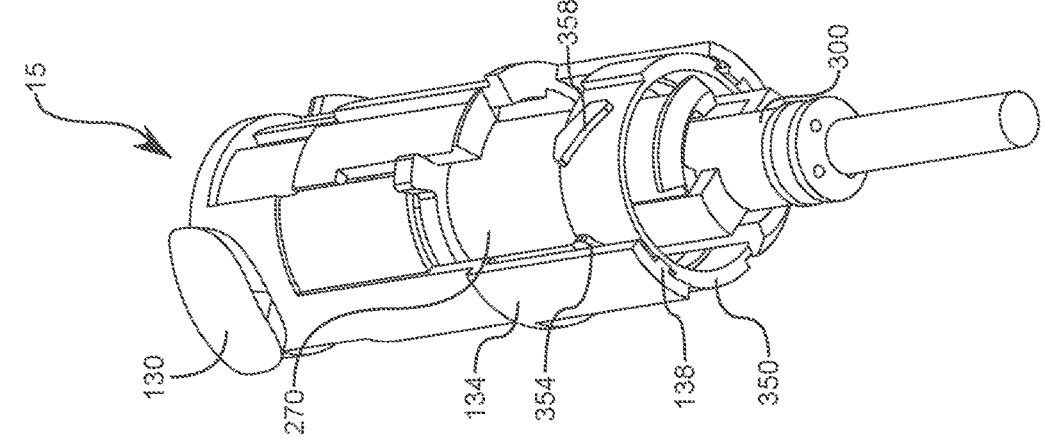
Figure 6A:
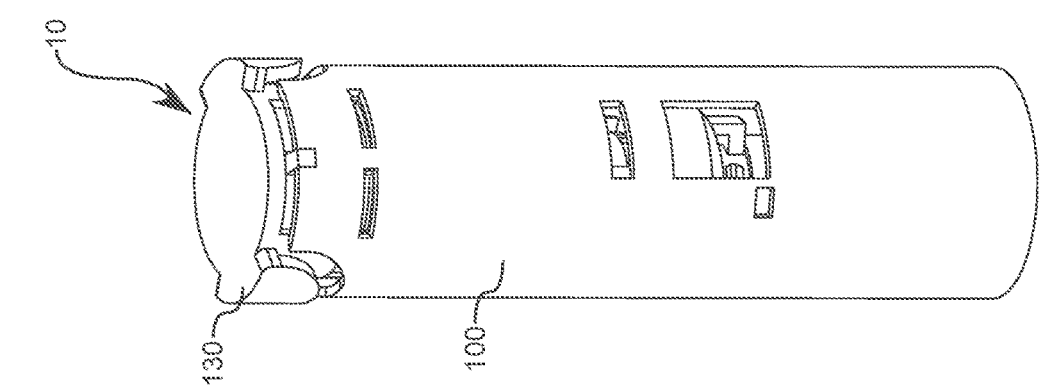

In reference to FIGS. 6A-F, shown is various stages of a mixing operation and the associated actuation associated therewith. As shown in FIG. 6A, the auto injector 10 will be changed from a stowed state by pulling upward on a telescoping component 130 or in other words exerting a tensile force between the telescoping component 130 and the housing 100. The application of this tensile force acts as a first trigger mechanism and causing the telescoping component 130 to translate axially with respect to the housing. The telescoping component 130 includes one or more extensions 134 which extend into the housing 100. The extensions 134 then further include a protrusion 138, which engages and interacts with the cam ring 350 of the movable body. The cam ring 350 includes a mixing cam ramp 354 wherein axial extension of the telescoping component, causes an upward motion of the protrusion 138 which in turn causes a rotation of the cam ring 350 as well as the movable body 300. The cam ring 350 can then further include an inward radial protrusion 352 which rests on a stop 274 of the vial sleeve 270 in a stowed state. The rotation imparted to the cam ring 350 by the protrusion 138 causes the inward radial protrusion 352 to rotate off of the stop 274 and into a channel 272 which allows for axial translation of the movable body with respect to the first vial and the vial sleeve 270. This radial translation can be effectuated by a biased mixing spring 40 which pushes the movable body 300 upward upon rotation of the inward radial protrusion 352 off of the stop 274 and into the channel 272.

In the embodiments shown, the drug delivery and mixing device 10 or 20 can include a mixing spring 40 disposed between the movable body 300 and the vial sleeve 270. This spring is initially biased so as to maintain the inward protrusion 352 onto the stop ledge 274 so as to maintain the device in a locked and unmixed stowed state. Upon pulling of the telescoping component 130 the torsional bias is overcome so as to rotate the inward protrusion 352 from the ledge 274 and into the channel 272. At this point the cam ring 350 is allowed to translate upward. This upward translation allows a simultaneous release of the needle shield 150, arming of a second trigger, and mixing of the various drug components by displacing the contents of the first vial into the second vial, as discussed above.

Now with reference to FIGS. 7A-G, shown is a partial perspective view of an auto-injector 10 which illustrates a concurrent step of mixing and extending the needle shield 150. In the illustrated embodiments, the extension of the needle shield 150 also serves as an indicator that the device is armed, wherein the movable body 300 is extended completely upward thus displacing the first component from the first chamber to the second chamber, which complete upward displacement simultaneously allows for extension of the needle shield thus signifying an injection-ready state.

Figure 7D:
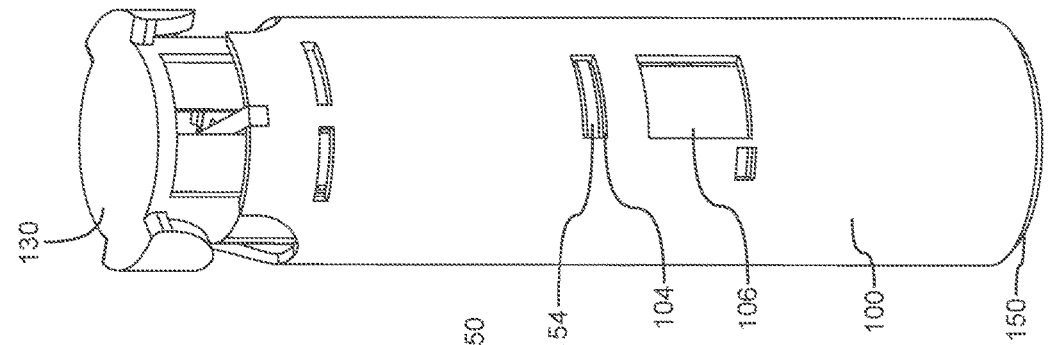
FIGS. 7A-G illustrate various stages of an arming and needle shield extension mechanism and process which is applicable to either of the portable drug mixing and delivery devices illustrated in FIGS. 1A-E or FIGS. 2A-E.
Figure 7C:
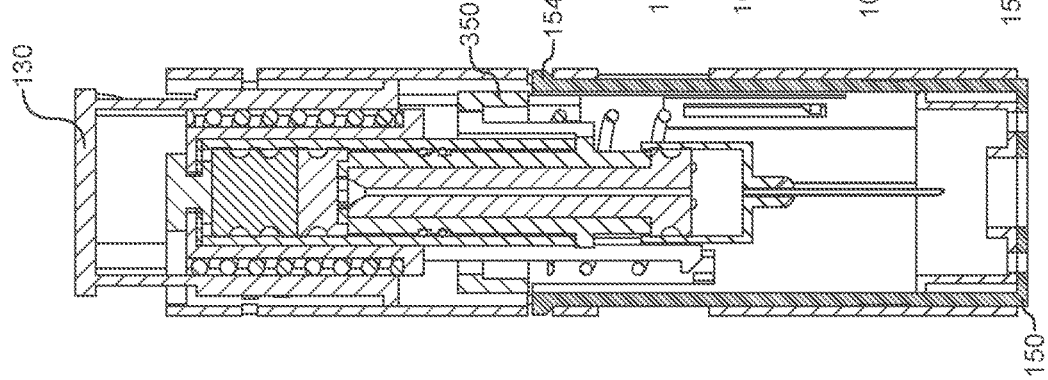
Figure 7B:
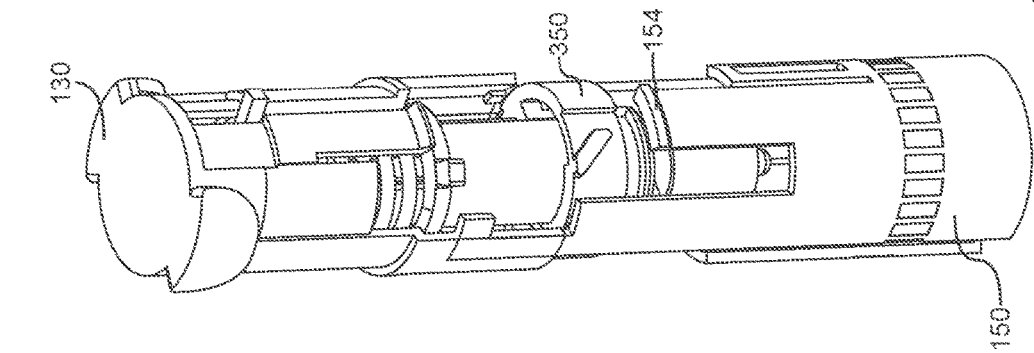
Figure 7A:
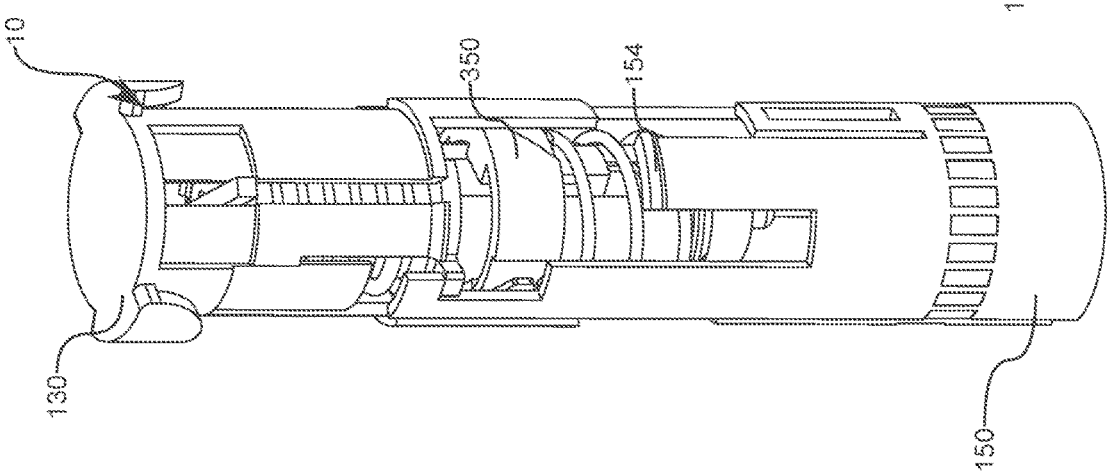
Figure 7G:
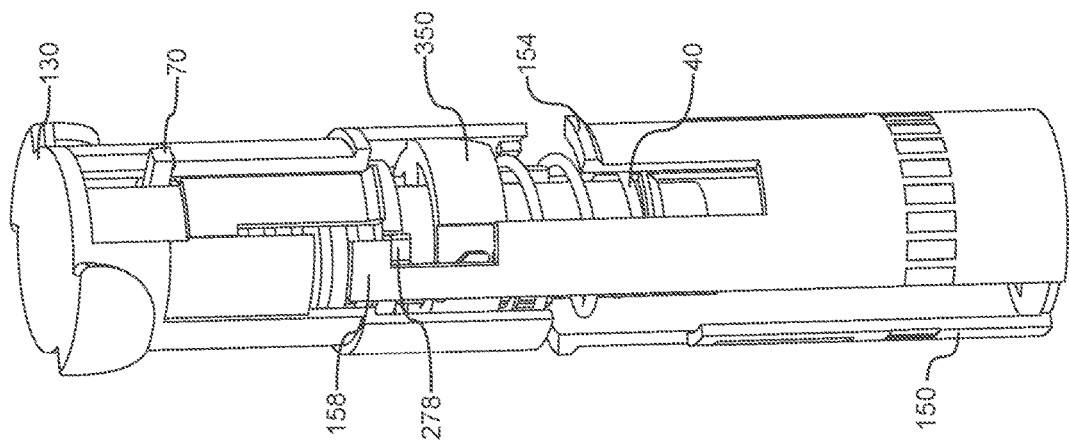
Figure 7F:
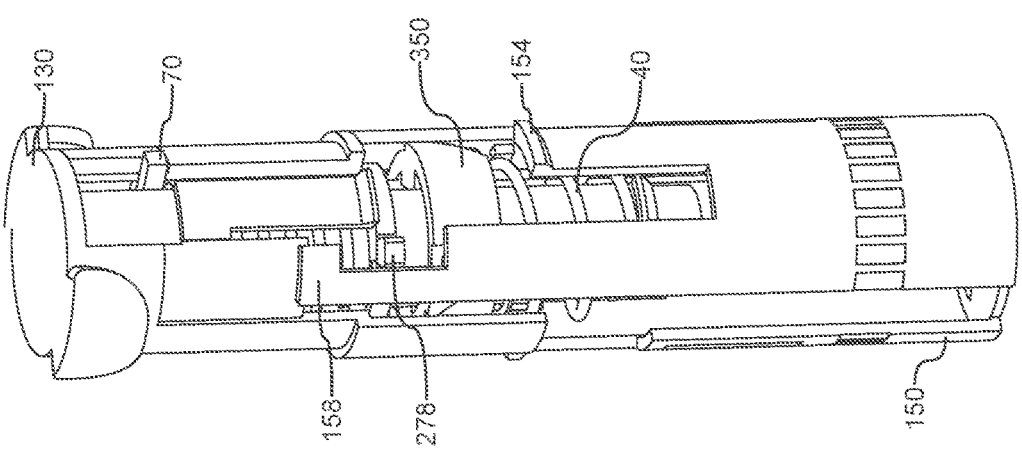

In the stowed state, the cam ring 350 is initially in an interference position with a one or more radially outward oriented protrusions 154 provided on one or more arms of the needle shield which extends into the housing 100. The housing has corresponding notches 104 provided in a sidewall, which notches are configured to receive the one or more outward oriented protrusions 154 in a stowed state. In this stowed state, the cam ring 350 abuts against the back side of the outward oriented protrusions 154 which provides interference to, and thus prohibits the outward oriented protrusions 154 from deflecting inward and allowing the needle shield 150 to be extended. However, by rotating the cam ring 350, as discussed above, by pulling the telescoping component 130, as shown in FIG. 7A, the cam ring is then allowed to translate upward, moving the movable body, and corresponding plunger into the first chamber.

Figure 7E:
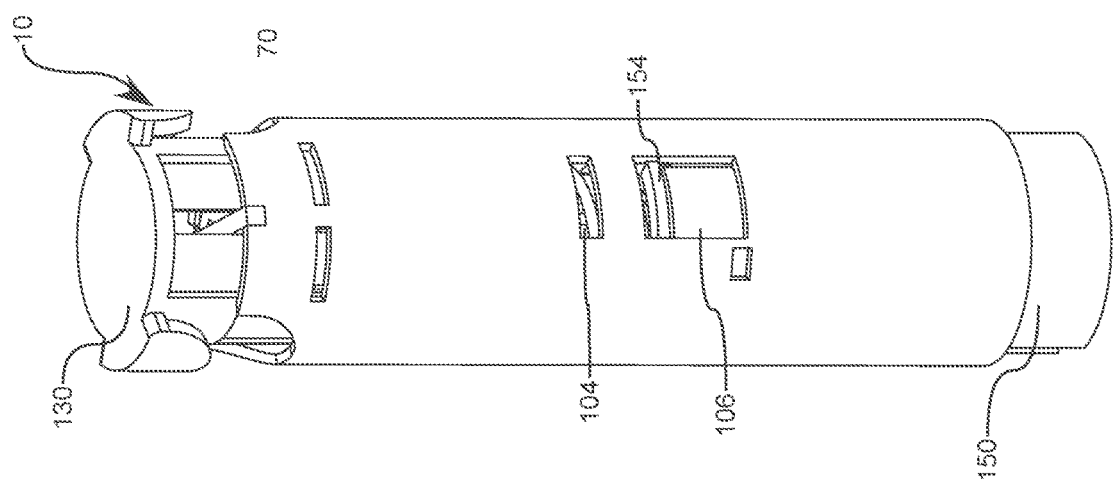

In the embodiment shown, the cam ring has a sufficient width such that, one the movable body is pushed completely upward, the lower edge of the cam ring then clears the upper edge of the extensions on which the outward oriented pair of protrusions 154 resides, and the needle shield spring 50 provides a requisite force to cause the inward deflection of the outward oriented pair of protrusions 154 and the outward oriented pair of protrusions 154 can slide downward in an extended position into a lower slot 106 in the sidewall of the housing, as shown in FIG. 7E. It will be appreciated that the lower slot 106 is larger so as to allow depression and extension into a locked outward position during the injection step.

Further, the needle shield 150 can be provided with an upper arm extension and hook 158 which initially interfere with one or more corresponding protrusions 278 provided on the vial sleeve 270, which interference prevents the needle shield 150 from being extended prior to completion of the mixing step. The hook 158 can also be configured so as to interfere with an interior portion of the housing after injection, so as to prevent the needle shield from being fully removed from the housing after injection and any potential contamination by the used needle thereafter.

Once the needle shield 150 is extended such that the outward oriented pair of protrusions 154 are pushed into the lower slot 106, a subsequent depression of the needle shield is configured to function as a second trigger mechanism which triggers release of energy stored in an injection spring, shown as spring 60 in FIG. 3, which actuation will be discussed in further detail below.

In order to fully understand the actuation, reference will now be made to FIGS. 8A-B which illustrate the various cam ramps of the cam ring 350 which effectuates movement of the movable body 300. FIGS. 8A-B illustrate the mixing cam ramp 354, which interacts with the inward protrusion of the telescoping component as discussed above, so as to initiate rotation, and thus mixing. The cam ring 350 is also provided with an injection ramp 358 which facilitates a second counter rotation of the cam ring 350 in an injection step upon depression of the needle shield back into the housing after initial extension. It will be appreciated that initially the cam ring 350 and movable body 300 rotate independently of the vial sleeve 270 and the first vial 200 in the first mixing step, however, because the cam ring protrusion 352 slides into the channel 272 of the vial sleeve, any further rotation causes rotation of both the vial sleeve and the movable body together because the cam ring protrusion 352 interferes with the sidewalls of the channel 272 within a small tolerance as shown in FIG. 6F. Thus, rotation of the cam ring 350 in the second actuation or injection step causes rotation of the entire mixing assembly.

This second actuation rotation is effectuated by providing another radially inward oriented protrusion 162 on an inner surface of the needle shield 150 which interacts with another cam ramp of the cam ring 158 Upon completion of the mixing step, another secondary actuation occurs upon completion, wherein the cam ring has moved sufficiently upward such that the needle shield can be extended. In this extension process a few simultaneous actions are occurring during the extension. One action is that a second cam ramp 357 engages with an inward protrusion 162 of the needle shield, the relative axial motion causes the cam ring to simultaneously re-load a small amount of energy into torsional component of the mixing spring 40, and as the inward protrusion travels past the cam ramp 357 and below the protrusion forming the second cam ramp 357, the spring is unloaded again thus bringing the drug mixing and delivery device into the armed and mixed state by aligning the inward protrusion 162 with a bottom portion of the opposing cam ramp 358. At this point, the needle shield 150 acts as a second trigger mechanism which can be depressed to initiate injection. The depression then causes the inward protrusion 162 to engage with cam ramp 358, on the opposing side of the same protrusion forming cam ramp 357, so as to impart an opposing rotation to the mixing assembly and thus trigger injection which will be discussed in more detail below by releasing the mixing assembly from a retaining hanger, which will be discussed in more detail below.

Figure 10D:
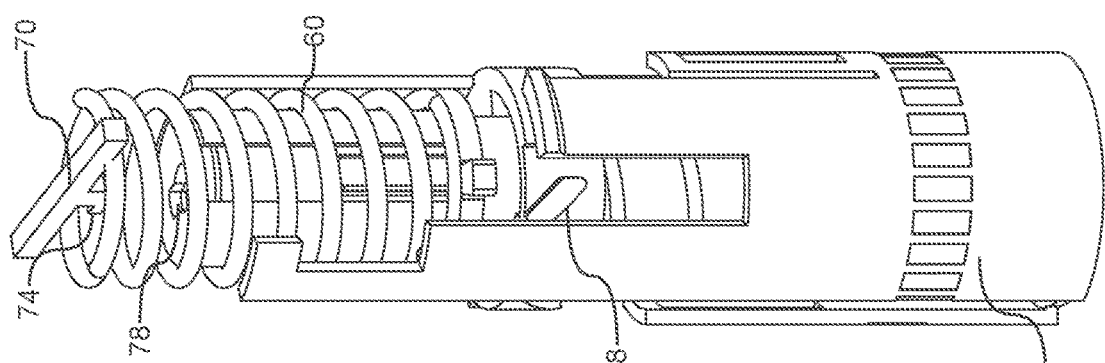
FIGS. 10A-D illustrate various stages of a firing mechanism and process which is applicable to either of the portable drug mixing and delivery devices illustrated in FIGS. 1A-E or FIGS. 2A-E.
Figure 10C:
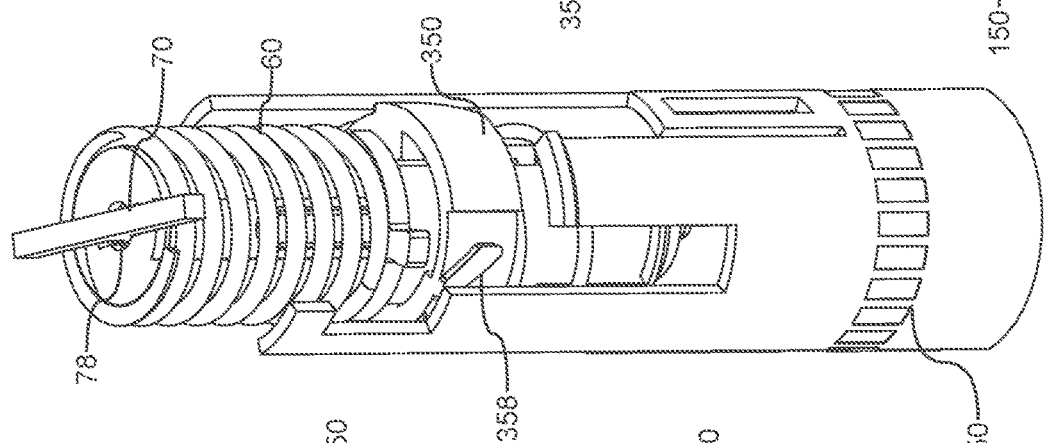
Figure 10B:
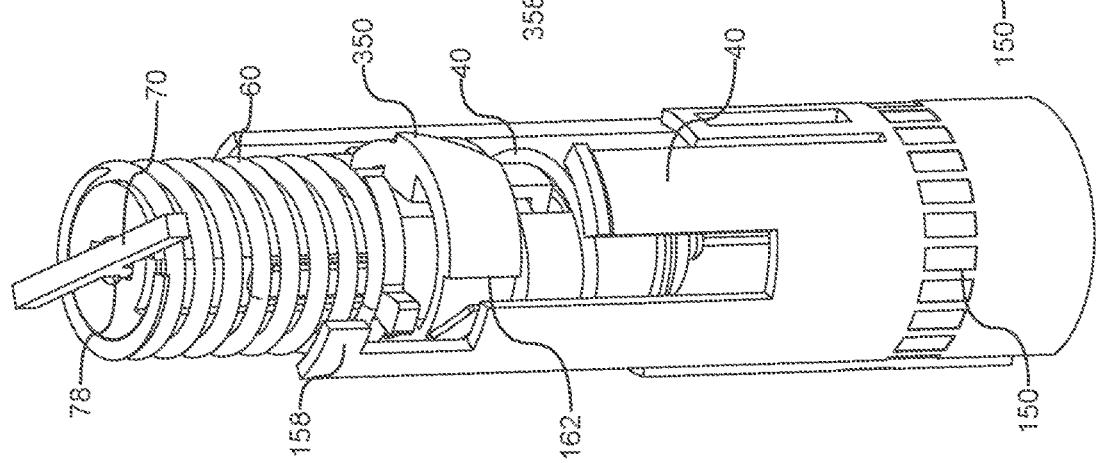
Figure 10A:
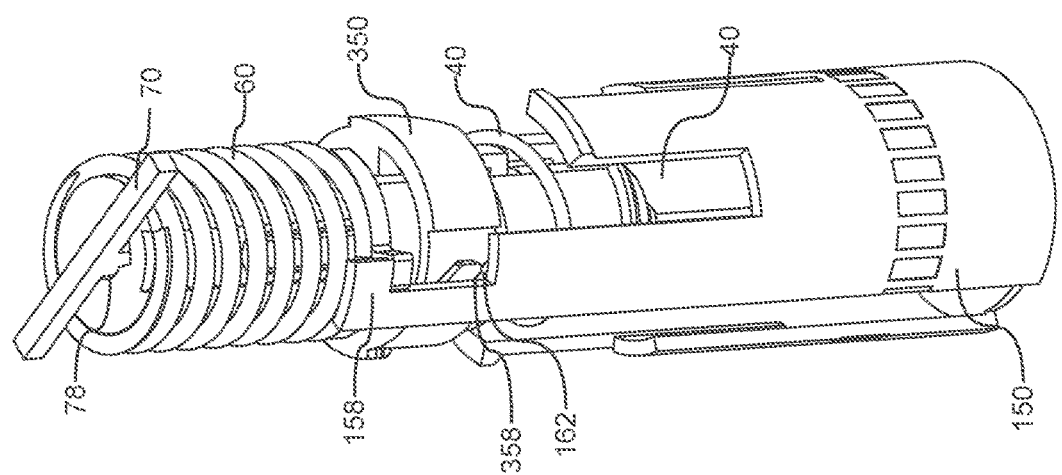

As discussed above, a torsional force component of the mixing spring which is released upon activation of the mixing step, allows the cam ring 350 to translate, and then realign for second trigger arming and subsequent needle shield depression and injection. This alignment force of the torsional component is configured to come to rest in an aligned position between the radially inward oriented protrusions 162 and a bottom portion of the injection cam ramp 358. In this manner, a depression of the needle shield 150 causes a counter rotation of the mixing assembly, in particular with regard to the housing 100 and the hanger 70 supported thereby. As shown, an upper portion of the mixing assembly includes a keyed slot or hole 78 which is provided in an unaligned position with a keyed protrusion 74 of the hanger 70. The rotation of the mixing assembly, through depression of the needle shield 150, causes the keyed slot 78 to move from an unaligned state, as shown in FIGS. 10A-C, into an aligned state as shown in FIG. 10D, wherein upon alignment, the injection spring 60 is allowed to release a portion of energy stored therein, forcing the mixing assembly to translate axially downward until the needle barrier 412 abuts a bottom portion of the needle shield, and wherein the needle is translated out through and piercing the barrier until it extends past the injection end of the device, and wherein the second vial 400 finally abuts a bottom portion of the needle shield wherein the downward force causes the second plunger 312 to displace the mixed drug from the second vial and into the injection site.

It will then be appreciated that the needle shield 150 is still biased outward and will automatically re-extend to cover the needle as the device is pulled away from the injection site. After injection is completed, the needle shield 150 can then be caused to disengage from the stops 278 of the mixing assembly and extend into a fully locked outward position.

Figure 11:
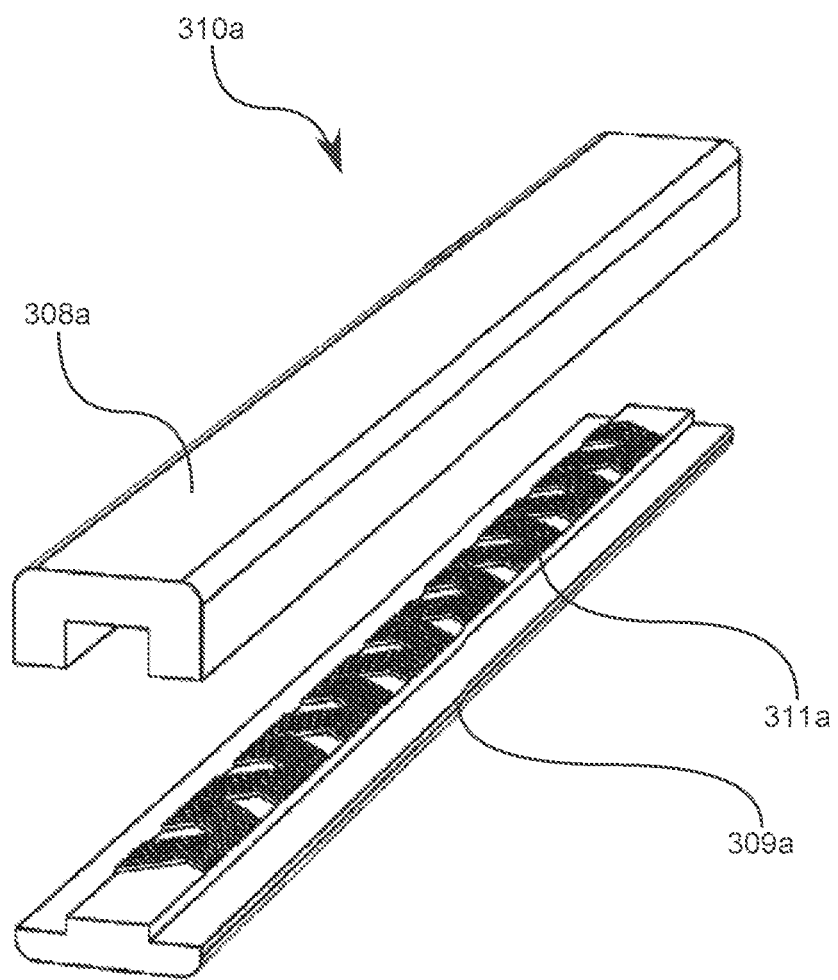
FIG. 11 illustrates a fluidic channel insert which is adaptable for use in either of the portable drug mixing and delivery devices illustrated in FIGS. 1A-E or FIGS. 2A-E.

FIG. 11 illustrates a fluidic channel insert 310a which can include a plurality of internal raised features 311a. In some embodiments the fluidic channel insert 310a can be formed of opposing plates 308a and 309A wherein the raised features 311a can be machined or otherwise provided through laser or chemical etching processes on the opposing interior surfaces and then assembled to form a singular insert with a central cavity having the features on the exterior surfaces after assembly. This insert can then be provided into the movable body so as to provide a fluidic channel having the desired configuration of raised features therein. These features can be manipulated so as to provide various flow characteristics, such as increased turbulence for purposes of reducing flow resistance, increasing flow speed, mixing characteristics, etc.

FIGS. 12-16D illustrate yet another embodiment of an auto injector 500 which utilizes various aspects of the present invention. Similar to the embodiments discussed above, the auto injector 500 utilizes a movable body which initially moves in an opposing direction to the injection direction, which motion is initiated by pulling on a telescoping end and axially translating a telescoping component with respect to the auto injector housing. Other similarities arise in the provision of a dynamic seal as well as a compression or squeeze chamber to allow upward translation of a displacement device until fluidic communication is established between separate and distinct chambers within the auto injector.

In this embodiment the auto injector 500 is provided with drug mixing assembly 550, the mixing assembly 550 has a movable body in fluid communication with a first and second chamber. The first chamber or upper vial 618 can be configured to store a wet component. The mixing assembly can then be provided with an actuation device configured to cause the movable body 609 to enter a portion of the first chamber 618 during a first actuation process thus displacing the wet component stored therein into a second chamber or vial 614 during a second actuation process. As the movable body 609 enters the first chamber 618, it displaces the wet component through a fluidic channel 621 provided within the movable body 609, and into the lower or second vial 614. In some embodiments a dry powdered material containing at least one pharmaceutically active ingredient can be stored either in the fluidic channel or within the second vial. In some configurations the fluidic channel can effectively function as a third dry chamber wherein the first vial, the dry chamber, and the lower vial combine to form a total of three chambers.

In one embodiment, fluidic communication can be enabled with the first chamber and the dry chamber through a valve, burst membrane, orifice or other mechanism and/or opening. As illustrated, the aperture of the fluidic channel is initially sealed against the upper seal 610 thus preventing premature mixing of the wet and dry components but the translation of the movable body 609 into a portion of the first chamber causes an aperture of the fluidic channel to translate sufficiently upward so as to establish fluid communication, i.e. thus opening a valve. Once fluid communication is established the wet component stored in the first chamber 618 is permitted to flow through the fluidic channel 621 and into the second or lower vial 614, and cause the dry medicament to combine and mix with the wet component as it flows into the second or lower vial.

In a second motion and/or actuation step, the mixing assembly 550 is driven downward, which motion then causes the movable body 609 to translate into the second chamber 614 and subsequently displace the mixed component through a delivery assembly, such as through a needle 623 or jet (needle-less system) and into an injection site or other delivery site.

In some embodiments of the drug mixing system, the movable body 609 can be provided with a mixing volume for retaining a dry medicament component. This mixing volume can be a dry chamber, a dry channel, or a separate mixing chamber.

In yet additional embodiments of the drug mixing system, the volume of the movable body includes a separate fluidic channel assembly 621. In some such embodiments the fluidic channel can be provided with internal features designed to promote mixing. In yet additional embodiments, the fluidic channel is a micro-fluidic channel. In some such embodiments, the fluidic channel can be provided with tortious path having numerous bends. In yet further embodiments, the fluidic channel defines a volume for mixing the wet component with the dry medicament. In yet additional embodiments, the tortious path creates turbulent flow for mixing the wet component with the dry medicament. In some such embodiments, the series of structures, walls, or grooves in the walls of the mixer body and or channel can help promote mixing of the dry medicament and defining the volume for mixing the wet component with the dry medicament.

In some such embodiments, at least one of the dimensions in the channel is less than 5 mm. In an embodiment, at least one of the dimensions in the channel is less than 2 millimeters. In an embodiment, at least one of the dimensions in the channel is less than 1 millimeters. In an embodiment, at least one of the dimensions in the channel is less than 0.5 millimeters. In an embodiment, at least one of the dimensions in the channel is less than 0.25 millimeters. In an embodiment, at least one of the dimensions in the channel is less than 0.1 millimeters. In an embodiment, at least one of the dimensions in the channel is less than 0.05 millimeters. In an embodiment, the Reynolds number in the fluidic channel is less than 2300. In an embodiment, the Reynolds number of the fluidic channel is less than 100. In an embodiment the Reynolds number in the fluidic channel is 2300 or greater. In an embodiment, the channel further includes a plurality of grooves formed therein, wherein the grooves promote mixing when a wet component flows by and/or near the grooves. In an embodiment the mixing assembly further includes bends in the channel wherein the bends promote mixing when a wet component flows by the bends. In an embodiment, the mixing assembly includes obstructions in the flow path wherein said obstructions promote mixing when the wet component flows by the obstructions.

In one drug mixing system a powdered material or medicament can be loaded into a fluidic channel 621. In another drug mixing system a powdered material is loaded into a ferrule 625. In one embodiment this ferrule 625 is designed as an integrated feature inside the fluidic channel 621, while in other configurations the ferrule 625 is positioned adjacent the fluidic channel 621. Powder or medicament can be filled directly into the ferrule 625 using several methods including vibration techniques, auger, volumetric fill, or, lyophilizing, spray drying, vacuum drying or filling of pellets, or other method of filling powder doses. This ferrule 625 can be made of plastic, and/or rubber, and/or glass and/or any other suitable material. In another embodiment, the ferrule 625 can be provided as a removable piece that can be filled outside the fluidic channel using a variety of volumetrically dosing or mass based powder-dosing tools. Once the ferrule 625 is filled with powder, separate from the mixing assembly 550, the ferrule 625 can be placed inside the mixing assembly 550 and secured as a permanent or semi-permanent fixture.

The features of the ferrule 625 are designed such that there are two holes, and/or orifices and/or regions where fluid may enter and/or exit the ferrule. In one embodiment there is one inlet and one outlet where the inlet is defined by the region where fluid will enter the powder pocket and come into contact with the powdered material and create a mixed solution or partially-mixed solution. A mixed solution for the purpose of this invention is defined to be at least one liquid component and at least one powdered material that is partially mixed together and/or fully mixed together and/or where the powdered material is partially dissolved in the liquid component and/or fully dissolved in the liquid component. In another embodiment the liquid component can be two liquids or more. In another embodiment the powdered material can be two powdered materials or a blend of powdered materials.

The outlet of the ferrule is defined by a hole, or orifice, or region where the mixed solution will pass out from the ferrule and into another chamber, i.e. the lower vial 614. In one embodiment the solution will pass out of the ferrule as a partially combined fluid and/or mixture with the powder in the powder pocket. This mixed solution can exit the outlet and fill another chamber directly. In another embodiment, this mixed solution can pass through to a second chamber by first traveling through a fluidic channel 621. In one embodiment, this channel can be straight with a circular cross-section. In another embodiment this channel can be straight with a non-circular cross-section. In another embodiment this channel can be non-straight with a circular cross-section. In another embodiment this channel can be non-straight with a non-circular cross-section. In one embodiment, the channel can have and or create bends or turns in the fluid path. In one embodiment the fluid path can have a serpentine shape, or a spiral shape, or some other shape, for example, winding back-and-forth and/or have features, ridges or groves inside the channel, which creates a tortious path or some combination of all previous embodiments.

In one embodiment, the fluid inlet hole can have a larger diameter than the fluid outlet hole. In another embodiment the fluid inlet hole can have a larger cross-sectional area than the outlet hole. In another embodiment, the fluid inlet hole can be sized to be approximately the same size as the fluid outlet hole. In one embodiment the side-wall of the ferrule can taper uniformly down to the fluid outlet hole. In another embodiment, the ferrule can include differing geometries where those geometries can be conical, hemispherical, or rectangular wedge shaped. The sidewalls of the ferrule can be textured to increase or reduce powder-ferrule interfacial friction the help with powder filling and potentially promote mixing of the liquid and powder inside the ferrule.

In one embodiment the outlet hole of the ferrule can be covered by a sealing structure or partially sealed structure which can be used to retain powdered material inside the powder pocket during a filling operation or during storage. In one embodiment this sealing structure can also prevent fluid flow until the device was actuated which resulted in a change to the sealing structure, which would allow fluid to flow through the powder pocket.

In one embodiment, as illustrated, a sealing structure 610 can be provided over the inlet of the ferrule but not the outlet. In one embodiment there is a sealing structure over both the inlet and the outlet. In some embodiment the ferrule can be formed from a soft elastomer and the sealing structure is a small orifice that remains constricted until pressure from fluid flow forces the orifice to open and allows a partially mixed fluid of powder and solvent to flow.

The promotion of mixing inside the ferrule can come from the fluid resistance created by the outlet hole being smaller than the inlet hole forcing liquid to create eddies which fold back on themselves to cause chaotic and/or turbulent flow by which the powder may mix fully and/or dissolve fully and/or mix partially and/or dissolve partially with the liquid entering the ferrule.

The ferrule can also be formed from metals and metal alloys (such as stainless steel), plastics (such as polypropylene, polyethylene, PEEK, COP, PET, PLA, etc), elastomeric materials (such as silicone, butyl rubber, or chlorobutyl rubbers), materials such as glass, or other materials that are coated with a PTFE coating or some other coating.

In an embodiment, at least some of the mixing occurs in the ferrule.

In one embodiment, the promotion of mixing inside the ferrule can be increased by structures inside the ferrule including but not limited to ridges, grooves, bumps, herringbone structures, and so forth that help to create a tortious path.

In one embodiment, the powder is filled into a well and/or blister and/or some other receiving region that holds the powder. In one embodiment the powder is introduced into a holding region as a liquid and then lyophilized and/or vacuum dried and/or dried in some other way inside the powder holding region.

In the illustrated embodiment, the fluidic channel 621 can be provided with a mixing volume for retaining a dry medicament component prior to mixing with a wet component to form a wet medicament solution or mixture. In this embodiment, the fluidic channel 621 can be sized to define a hollow volume corresponding in volume to the dry medicament component that is to be placed or received therein. As displayed, the upper vial 618 can be provided with selective fluidic communication, through the fluidic channel within the movable body 609, to the lower vial 614. In certain embodiments the movable body 609 can be formed of multiple parts. As illustrated the movable body 609 can be provided with a separate fluidic channel insert, or the fluidic channel can be unitarily formed within the movable body.

Once a wet component passes from the first chamber 618 and into the fluidic channel 621, it can then be received by the lower vial 614 and subsequently passed through a needle 623 or other delivery assembly into the injection site.

In yet additional embodiments the second chamber 614 can be configured to carry or store a second medicament or component, wherein the first chamber carries the first wet component to mix with the dry medicament in the dry chamber (having a fluidic channel) disposed in the movable body prior to mixing with the second wet component in the second chamber.

In this embodiment, the system includes a needle assembly in fluid communication with the second chamber and a safety. The needle assembly and the second chamber are selectively movable independently or as a single unit relative to the housing. The system has a second actuation device that causes the needle assembly to be exposed or protrude from the housing and capable of injecting a wet medicament mixed in the fluidic channel. The safety is movable from a first safety position to a second position prior to the activation of the actuation device.

In this embodiment of a drug delivery system the system can include a housing having an extension component that is movable relative to the housing and causing the effective length of the housing to have a larger dimension. The extension component may be a telescoping component, an unfolding component, re-attachable or other lengthening/widening type component. In one embodiment, the extension component when activated and/or lengthened allows the first actuation device to cause the movable body to move into the first chamber. In one embodiment the extension component is attached to a removable sleeve that extends the injector fully and then releases, or is ripped away from the auto injector.

While this embodiment can be normally stored in a compact state, it is ready for activation upon a pulling action wherein the user pulls the frame extension cap 601 backwards and the needle shield 606 pops out of the device. This device design enables storage in a small footprint but extends during use, making it larger and thus easier and safer to handle.

In this embodiment, the telescoping component, i.e. the frame extension cap 601 moves laterally relative to the first housing in order to increase the effective interior space of the housing In the illustrated embodiment, the first chamber is collapsible, or in other words, the effective volume can be selectively reduced. In this embodiment, the movement of the movable body 609 reduces the volume of the first chamber.

In the illustrated embodiment the mixing assembly 550 can incorporate a valve mechanism that opens the fluid path between the upper and lower vials thus allowing for a mixing between the wet and dry components. Mixing within this concept is initiated via a pulling of an extension cap 601 relative to the outer housing 604. The pulling causes a rotation of an unlock ring 611 within the internal frame. The rotation of the unlock ring 611 causes an outward deflection of clip arms of the mixing spring clasp 622 until release of the mixing spring 619. The mixing spring 619 is coupled to the movable body 609, wherein release of energy stored in the spring 619 results in an upward translation of the movable body 609 into the upper vial 618 which simultaneously establishes fluidic communication between the upper and lower vials and allows for mixing process that operates independently of user action once initiated.

The mixing process begins when the movable body 609, held in place by the mixing spring clasp 622, is released. As the user pulls upwards on the frame extension end cap 601, the frame extension cam 602 rotates the unlock ring 611. The unlock ring 611 has a ramped exterior surface which interferes with locking arms of the mixing spring clasp 622. these locking arms are flexed outward by the rotation of the unlock ring 611 until a clearance is established between a notch on the movable body 609 and these locking arms. This clearance allows for the mixing spring 619 to unload thus releasing the movable body 609 and causing it to travel upward into the upper vial 618.

The spring clasp 622 in one embodiment is envisioned to be constructed from stamped metal to avoid creep relaxation in plastic parts. In one embodiment this part is to be made out of plastic and/or some other composite material, and possibly integrated into the outer housing 604 or internal frame 603.

With the mixing spring 619 expanding, the movable body 609 moves upwards, initiating the mixing process contingent on some compliance either in the upper vial 618, or in the movable body 609. It will be appreciated, as discussed above, that most fluids are incompressible, as such a compressible substance or material is provided within, or in communication with, the upper vial 618. In the embodiment shown, an air pocket 650 is provided within the upper vial 618 which can compress so as to allow relative translation of the movable body 609 into the upper vial 618 until fluidic communication is established and the fluid is allowed to travel into the lower vial 614.

It will be appreciated that while the present embodiments illustrate an open air pocket 650 for allowing the movable body 609 to initially move into the upper vial 618 until fluidic communication is established, that the air pocket can also be contained within a compliant chamber using a flexible or compliant barrier in an upper portion of the vial, or alternatively upon the upper surface of the movable body 609 itself.

As discussed above, the wet component is allowed to flow into the opening in an upper portion of when the opening clears the top edge of the upper seal 610. At this point, the wet component is flushed through the fluidic channel 621 and/or ferrule 625 through and down into the lower vial 614.

It will be appreciated that because the mixing process is triggered by the release of the spring clasp 622 and the upward release of the mixing spring 619, that the mixing spring 619 is strong enough to compress the air pocket sufficiently to move the movable body 609 a sufficient degree so as to establish fluidic communication, and then push the liquid component through the fluidic channel 621 as well as expand the lower vial 614 sufficiently to receive the mixed drug and liquid.

Once the movable body 609 has fully depressed into the upper vial 618, thus reducing the effective volume of and pushing the fluid into the lower vial 614, the mixing assembly 550 is ready to deliver the mixed components from the lower vial 614 through the needle 623.

The injection actuation is provided by initially extending and then re-depressing the trigger/needle-shield 606, which as it is re-depressed, its upper arms cause an internal actuation, which as discussed below, will eventually release the injection spring 608. The release of the injection spring 608 is effectuated by the hanger stop retainer 607, wherein rotation of the rotating ring is effectuated by a subsequent depression of the needle shield 606 relative to the internal frame 603 and the mixing assembly 550.

The second actuation device involves the needle shield 606, which has a pair of extended arms that extend into the internal frame 603 and interact with the rotating hanger stop retainer 607. Depression of the needle shield 606 after initial extension causes the rotating hanger stop retainer 607 to rotate the hanger stop 616 relative to the hanger 617. In the illustrated embodiment, the second actuation device can include a pre-loaded spring which provides an injection force which causes the mixing assembly to be driven downward, abut against a bottom portion off the interior of the internal frame, thus causing the movable body to compress into and reduce the effective volume of the lower vial 614 and eject the mixed components through the delivery assembly.

The injection spring 608 itself is held in place by two pieces, the inner part of the hanger 617, connects to the lower face of the spring 608, while the hanger stop 616 is locked to the upper portion of the spring via a keyed hole. By rotating the hanger 617 relative to the hanger stop 616, the spring is released. In one embodiment the hanger 617 and the hanger stop 616 are made of resilient or spring steel. In another embodiment they are made of plastic or some other material. The rotating ring 607 can rotate, i.e. clockwise as shown, relative to the hanger stop 616, which is held rotationally via friction created by the injection spring 608 and the hanger 617. A protrusion on the side of the rotating hanger stop retainer 607 serves to receive a rotational force as imparted by the needle shield arms which function as the trigger/needle-shield 606 extends outward from the housing during the mixing phase. After the needle shield 606 initially clears this protrusion, flexible beams return the hanger stop retainer 607 back to its original position, with the protrusion above the needle shield 606. The device is then armed as is signaled by the initial extension of the needle shield 606.

In this position, the device is ready for activation upon re-depression of the needle shield. As shown, the trigger/needle-shield 606 includes a pair of arms having angled upper cam surfaces which are shaped in such a way as to cause the rotating hanger stop retainer 607 to rotate in response to an axial re-depression of the needle shield 606, i.e. move counter-clockwise as shown, moving the hanger stop 616) relative to the hanger 617. When the hanger stop 616 no longer interferes with the hanger 617, the injection spring 608 is released.

In the illustrated embodiment, the system can further include a needle assembly. The needle assembly and the second chamber 614 can be movable as one unit relative to the housing. The second actuation device causes the needle assembly to be exposed or protrude from the housing and capable of injecting a prepared drug that is disposed in the movable body as described below.

As described above, as the hanger 617 released, the entire mixing assembly 550 is propelled downward through the internal frame 603. As the mixing assembly 550 is propelled downward by the injection spring 608, the sterility barrier 615 is buckled and the needle 623 is inserted into the user. The injection spring 608 continues extending after the lower vial 614 has contacted the bottom of the internal frame 603, moving the movable body 609, with upper vial 618, downwards through the lower vial 614, injecting the mixed component through the needle 623.

In some embodiments, the dry medicament is stored in the lower vial 614, which can be powder filled or lyophilized within the lower vial 614. For this embodiment a space or spacer would need to be included between the lower vial and the mixing spring in order to position the inner plunger at a sufficient distance away from the inner floor of the lower vial in order to provide sufficient space/volume within which the dry medicament may be stored. This space enables some compression if needed. Structures to improve reconstitution and mixing may be present in the lower vial. This may function as both an embodiment of the spacer and provide improved mixing in the lower vial.

In one embodiment the trigger/needle-shield 606 doesn't extend and/or make itself ready to be pressed until the mixing process has finished; preventing an incomplete mix from being delivered to the user. In order to provide actuation the needle shield 606 can include a pair of snap arms which initially hold the needle shield in place relative to the internal frame 603. In one embodiment, after mixing has been completed, and the movable body 609 has moved to the back of the upper vial 618, the needle shield snap arms are free to flex inwards since the movable body 609 has moved sufficiently upward so as to provide clearance. This requirement of clearance between the movable body 609 and the inward flexion of the snap arms ensures that the trigger/needle-shield 606 doesn't fully extend until the mixing process has completely finished; this introduces a failsafe mechanism to ensure safe use of the device.

After delivery is complete, the user simply removes the device and the needle shield 606 extends, driven by the needle shield spring 605. Additionally, a lockout mechanism is envisioned in the internal frame 603 which can consist of a snap, not shown, wherein the snap is deformed by the downward motion of the mixing assembly 550 during injection, wherein upon injection the snap engages an extension of the needle shield 606 and thus prevents any further movement of the needle-shield 606 after it has been extended for the last time, hiding the needle.

In one embodiment, the mixing module can be assembled either in a sterile environment or aseptically and sterilized afterwards using a terminal sterilization process. The mixing assembly 550 includes an upper vial 618, upper seal 610, mixing spring 619, unlocking ring 611, threaded mixing container 620, fluidic channel 621, mixing spring clasp 622, mixing spring cover 613, lower vial 614, needle 623, and sterility barrier 615.

Additionally, a method of assembly is contemplated which includes various steps, which steps can include: Attaching the unlock ring 611 and mixing spring clasp 622 to the mixing spring cover 613, then the movable body 609 and mixing spring 619 are loaded into this assembly by snapping the spring clasp 622 in place. The lower vial 614 can be placed over the movable body 609 at this point, possibly at the same time as the fluidic channel 621 which has been filled with the dry component previously, is slid into the movable body 609. With this portion of the mixing assembly being assembled, the upper vial 618, can then be filled with the wet component and glued (or attached via other methods) to the mixing spring cover 613. The upper seal 610 can then be attached and properly placed by threading the threaded mixing container 620 into the mixing spring cover 613. By adding the needle sterility barrier 615 to this assembly, the mixing module is complete and can be handled in non-sterile environment, as the dry component, wet component, and needle are all sealed from the environment.

Figure 13A:
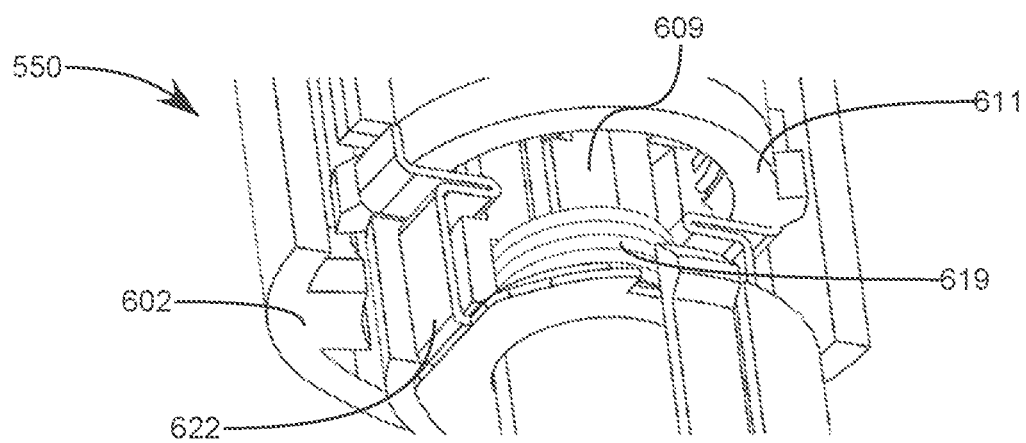
FIGS. 13A-C illustrate partial perspective cut away views of the portable drug mixing and delivery device of embodiment of FIGS. 12A-B which illustrate various mixing actuation steps which further illustrate various aspects of the present invention.
Figure 13B:
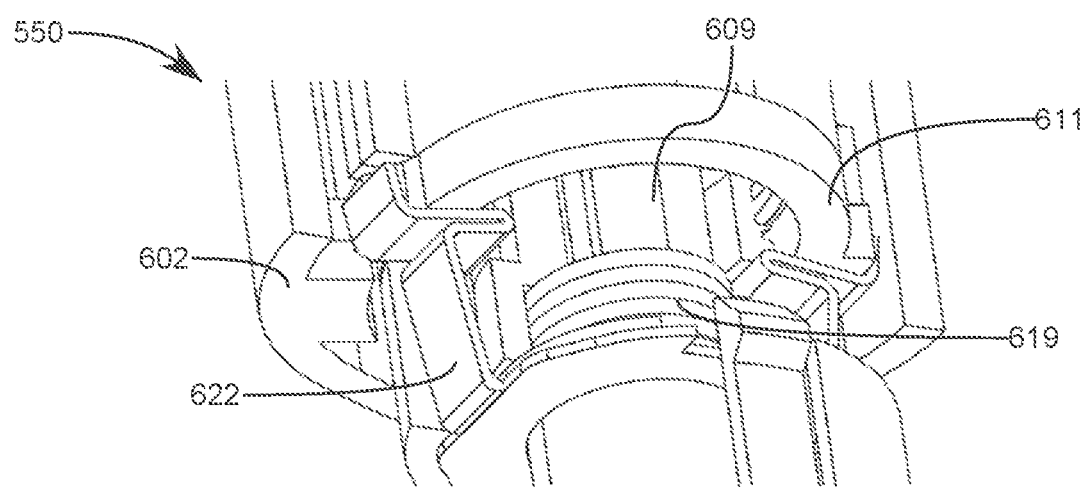
Figure 13C:
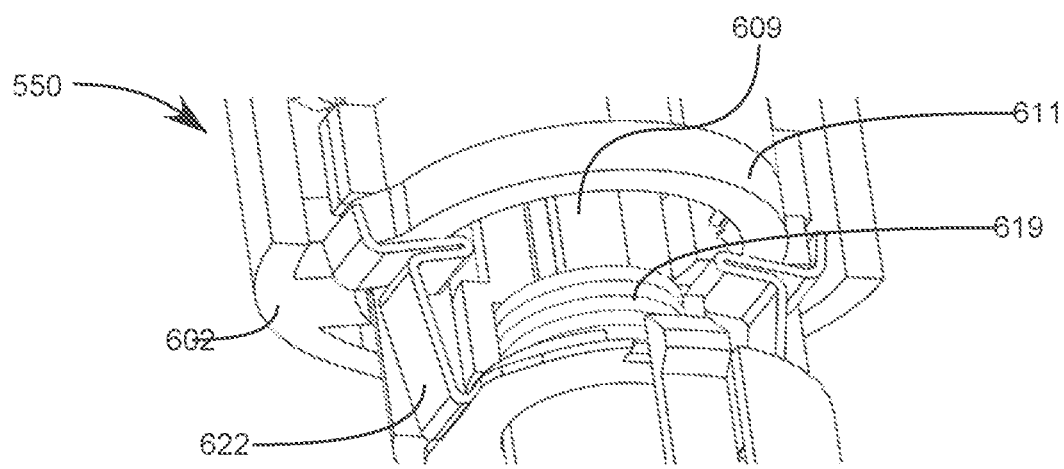
Figure 14A:
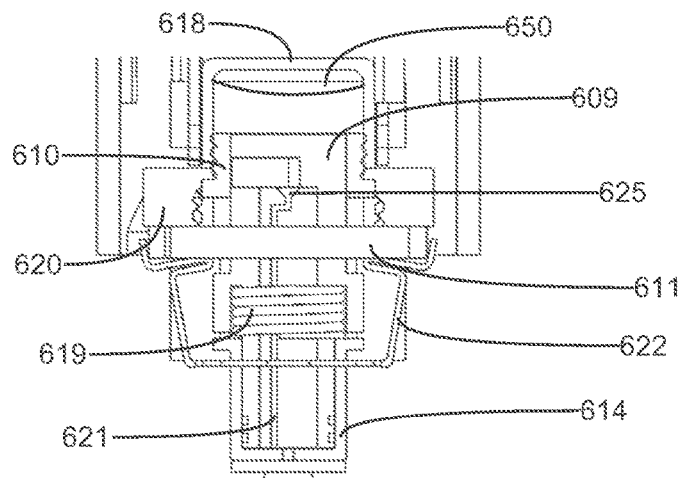
FIGS. 14A-C illustrate partial side cross-sectional views of the portable drug mixing and delivery device of embodiment of FIGS. 12A-B which illustrate various mixing actuation steps which further illustrate various aspects of the present invention.
Figure 14B:
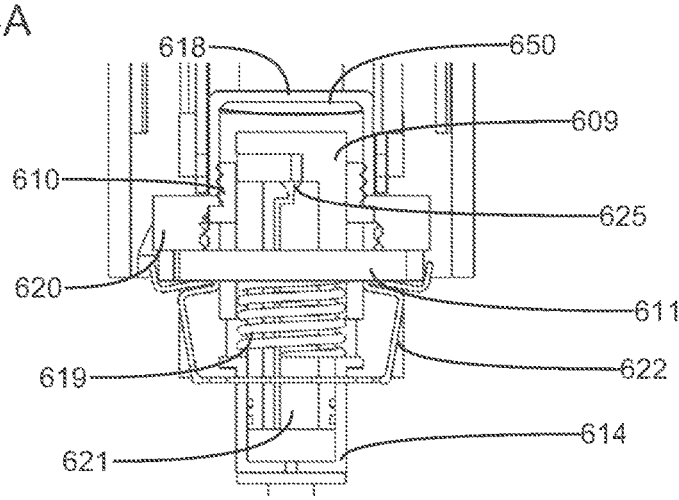
Figure 14C:
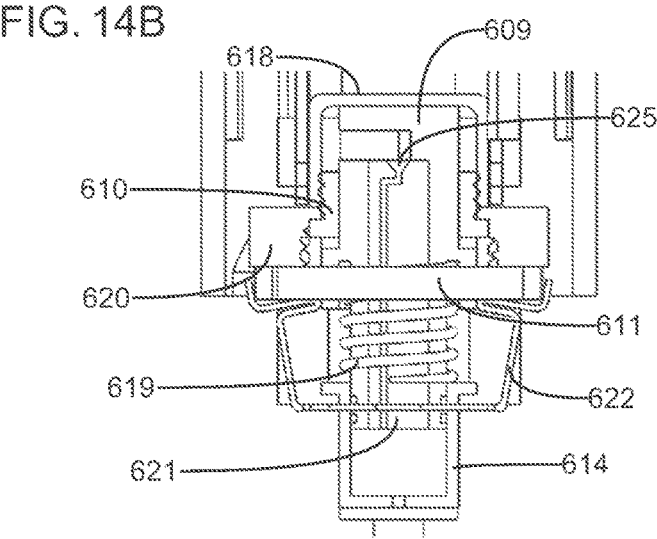
Figure 15A:
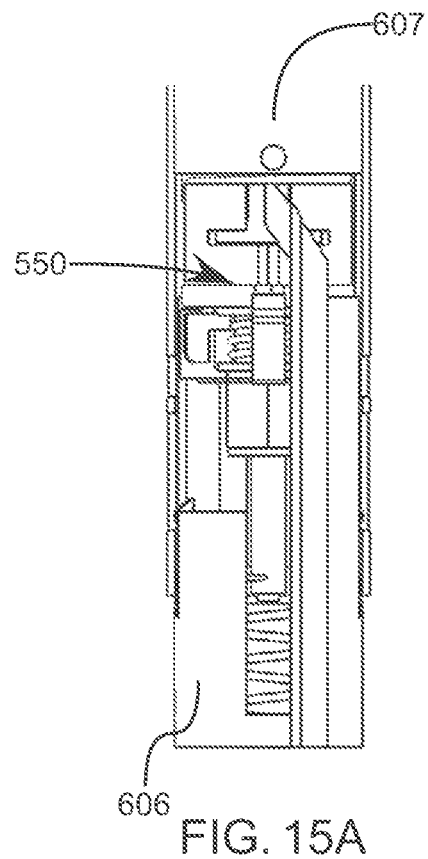
FIGS. 15A-C illustrate partial side cross sectional views of the portable drug mixing and delivery device of embodiment of FIGS. 12A-B which illustrate various mixing actuation steps which further illustrate various aspects of the present invention.
Figure 15B:
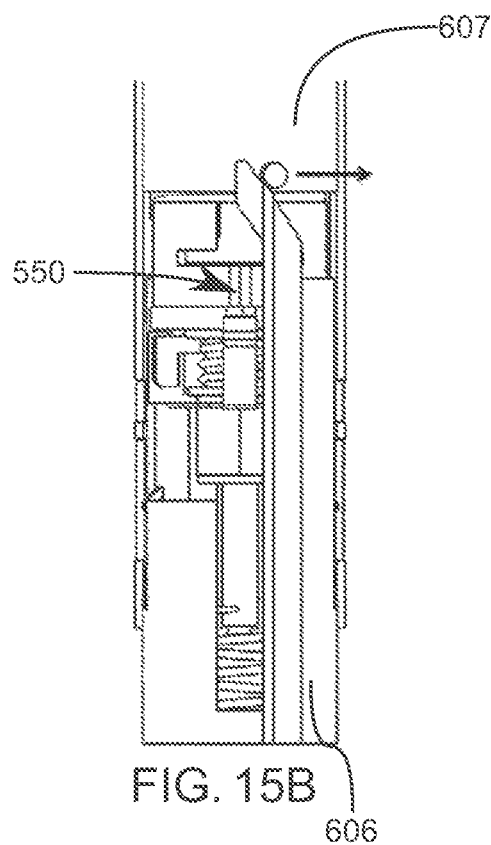
Figure 15C:
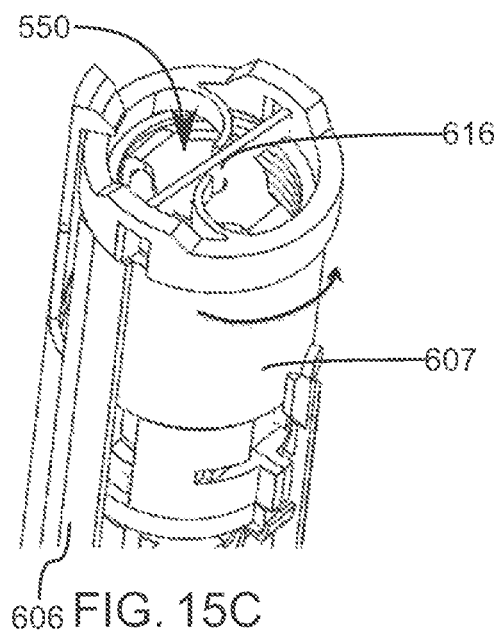

In one embodiment, the powder can be filled directly into the conical shaped reservoir 625 (powder pocket) shown in FIGS. 13A-B. In another embodiment, the powder can be filled into a ferrule that, once filled with powder, can then be placed inside the mixing assembly. In one embodiment, the removable powder pocket can be filled either by tareing out a mass weight of the powder pocket and then filling using some type of vibrational or auger filling tool or other volumetrically dosed methods of measuring and transferring the dose to the mixing and injection device. In another embodiment this powder pocket can be sized appropriately and volumetrically filled. In another embodiment, the reservoir can be filled with a pre-formed, fast-dissolving powder structure or lyophilized pellet. In another embodiment, the drug may be lyophilized into the powder pocket directly.

In some embodiments the dry powder module can be provided as a separate component from the movable body 609 in order to help facilitate filling with dry medicament and assembly. This also aids in allowing different drugs to be provided in various dosages so as to facilitate use in a variety of treatments and situations which is customizable to each individual drug application as well as each individual user's varying dosage requirements.

In yet additional embodiments the powdered material can be provided as a blend of one or more therapeutic agents and at least one pharmaceutically acceptable excipient.

In some embodiments, the therapeutic agent can be provided as glucagon, sumatriptan, alprostadil, or other erectile dysfunction medications, diazepam or anti-seizure medications, anti-coagulants, medications for tramatic brain injury, or antichemical weapon antidones, depo-provera, or other fertility medications, or Pegvisomant, Etanercept, Adalimumab, Infliximab, Bevicuzumab, Rituximab, Trastuzumab, Insulin Glargine, Enoxaparin, Pegfilgrastim, Glatiramer, Ranibizumab, Epoetin alfa, Methotrexate, Golimumab, Certolizumab, Abatacept, Avonex, Betaferon, Extavia, Rebif, Fraxiparine, Darbepoetin alfa, Filgrastim, Follitropin alfa, Urofollitropin, Lutropin alfa, Follitropin beta, Belimumab, Denosumab, Atropine, Edrophonium, Pralidoxime, Lidocaine (amiodarone), Midazolam, Morphine, Novocaine (procaine hydrochloride), Codeine, Albuterol, Amitriptyline, Dexamethasone Phosphate, Benzodiazepine, Docusate Sodium, Fluoxetine, Haloperidol, Fluoxetine, Haloperidol, Lactulose, Loperamide, Metoclopramide, In yet additional alternative embodiments the therapeutic agents can include Ondansetron, Hydrocortisone, Loratidine, Prednisolone, Cyanokit, Naloxone, Dimercaprol, Lorazepan, Phenobarbital, Cefazolin, an anti-inflammatory agent, anantimicrobial agent, an antifungal agent, an anti-parasitic agent, an anti-inflammatory agent, an anti-cancer agent, an agent for treatment of a cardiovascular disease, an agent for treatment of an allergy reaction, or a pain-relieving agent. In some embodiments, the therapeutic agent is an agent for treatment of an allergy reaction. In some embodiments, the agent is for treatment of anaphylaxis. In some embodiments, the agent is epinephrine.

Exemplified therapeutic agents include, but are not limited to, anti-inflammatory, antipyretic, anti-spasmodics or analgesics such as indomethacin, diclofenac, diclofenac sodium, codeine, ibuprofen, phenylbutazone, oxyphenbutazone, mepirizole, aspirin, ethenzamide, acetaminophen, aminopyrine, phenacetin, butylscopolamine bromide, morphine, etomidoline, pentazocine, fenoprofen calcium, naproxen, selecxip, valdecxip, and tolamadol, anti-rheumatism drugs such as etodolac, anti-tuberculoses drugs such as isoniazide and ethambutol hydrochloride, cardiovascular drugs such as isosorbide dinitrate, nitroglycerin, nifedipine, barnidipine hydrochloride, nicardipine hydrochloride, dipyridamole, amrinone, indenolol hydrochloride, hydralazine hydrochloride, methyldopa, furosemide, spironolactone, guanethidine nitrate, reserpine, amosulalol hydrochloride, lisinopril, metoprolol, pilocarpine, and talcetin, antipsychotic drugs such as chlorpromazine hydrochloride, amitriptyline hydrochloride, nemonapride, haloperidol, moperone hydrochloride, perphenazine, diazepam, lorazepam, chlorodiazepoxide, adinazolam, alprazolam, methylphenidate, myrnasipran, peroxetin, risperidone, and sodium valproate, anti-emetics such as metoclopramide, lamocetron hydrochloride, granisetron hydrochloride, ondansetron hydrochloride, and azacetron hydrochloride, antihistamines such as chlorpheniramine maleate and diphenhydramine hydrochloride, vitamins such as thiamine nitrate, tocopherol acetate, cycothiamine, pyridoxal phosphate, cobarnamide, ascortic acid, and nicotinamide, anti-gout drugs such as allopurinol, colchicine, and probenecide, anti-Parkinson's disease drugs such as levodopa and selegrine, sedatives and hypnotics such as amobarbital, bromuralyl urea, midazolam, and chloral hydrate, antineoplastics such as fluorouracil, carmofur, acralvidine hydrochloride, cyclophosphamide, and thiodepa, anti-allergy drugs such as pseudoephedrine and terfenadine, decongestants such as phenylpropanolamine and ephedorine, diabetes mellitus drugs such as acetohexamide, insulin, tolbutamide, desmopressin, and glipizide, diuretics such as hydrochlorothiazide, polythiazide, and triamterene, bronchodilators such as aminophylline, formoterol fumarate, and theophylline, antitussives such as codeine phosphate, noscapine, dimorfan phosphate, and dextromethorphan, anti-arrhythmics such as quinidine nitrate, digitoxin, propafenone hydrochloride, and procainamide, topical anesthetics such as ethyl aminobenzoate, lidocaine, and dibucaine hydrochloride, anticonvulsants such as phenyloin, ethosuximide, and primidone, synthetic glucocorticoids such as hydrocortisone, prednisolone, triamcinolone, and betamethasone, antiulceratives such as famotidine, ranitidine hydrochloride, cimetidine, sucralfate, sulpiride, teprenone, plaunotol, 5-aminosalicylic acid, sulfasalazine, omeprazole, and lansoprazol, central nervous system drugs such as indeloxazine, idebenone, thiapride hydrochloride, bifemelane hydrocide, and calcium homopantothenate, antihyperlipoproteinemics such as pravastatin sodium, simvastatin, lovastatin, and atorvastatin, antibiotics such as ampicillin hydrochloride, phthalylsulfacetamide, cefotetan, and josamycin, BPH therapeutic agents such as tamsulosin hydrochloride, doxazosin mesylate, and terazosin hydrochloride, drugs affecting uterine motility such as branylcast, zafylcast, albuterol, ambroxol, budesonide, and reproterol, peripheral circulation improvers of prostaglandin I derivatives such as beraprost sodium, anticoagulants, hypotensives, agents for treatment of cardiac insufficiency, agents used to treat the various complications of diabetes, peptic ulcer therapeutic agents, skin ulcer therapeutic agents, agents used to treat hyperlipemia, tocolytics, etc.

In yet additional embodiments the housing can be provided with a shroud, not shown, which initially covers the injection end of the auto injector and is selectively coupled to the housing, such that during the initial activation and mixing steps of extending the telescoping component the needle shield can be covered so as to prevent a user from being able to unintentionally cause a premature injection. The shroud can be interferingly engaged with the housing over the injection end wherein the extension of the telescoping component and a signaling of a completion of the mixing step also unlocks the shroud and allows it to be removed from the housing, thus allowing for initial extension of the needle shield and associated arming of the needle shield as the second injection step trigger.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention. Additionally, any features, structures, components, method steps which are discussed in reference to any one of the aforementioned embodiments are readily adaptable for use into and with any features of the other alternative embodiments discussed therein, with the understanding that one of ordinary skill in the art will be capable of assessing the ability and be capable of making such adaptations.

The invention claimed is:

1. A medication mixing and delivery device comprising:
   a housing;
   a first chamber, a second chamber, and a compression chamber located within the housing, wherein each chamber has a selectively changeable effective volume;
   a fluidic channel disposed between the first chamber and the second chamber;
   a seal positioned between the first chamber and the compression chamber;
   a movable body disposed between the first chamber and the second chamber;
   a mixing actuation device coupled to the movable body, wherein activation of the mixing actuation device facilitates:
      the selective reduction of the effective volume of the first chamber;
      the selective reduction of the effective volume of the compression chamber; and
      displacement of a liquid stored in the first chamber from the first chamber into the second chamber via the fluidic channel; and
   a delivery assembly configured to be in fluid communication with the second chamber.

2. The medication mixing and delivery device of claim 1, further comprising a dynamic seal separating the first chamber from the compression chamber, wherein the dynamic seal is configured to flex or translate axially.

3. The medication mixing and delivery device of claim 1, further comprising a mixing displacement device coupled to the movable body and wherein the mixing actuation device is activated through application of an axial tensile force, which axial tensile force releases a stop and allows the movable body and mixing displacement mechanism to translate in a first direction.

4. The medication mixing and delivery device of claim 1, further comprising an intermediate stopping mechanism wherein the intermediate stopping mechanism prevents fluid communication from the second chamber to the delivery assembly prior to activating a delivery actuation device.

5. The medication mixing and delivery device of claim 4, further comprising a needle shield assembly, the needle shield assembly further comprising a needle shield and a needle shield spring, the needle shield spring biasing the needle shield in an extended position.

6. The medication mixing and delivery device of claim 5, wherein the needle shield forms a part of the delivery actuation device, the delivery actuation device being configured to displace the movable body downward so as to displace the fluid out of the second chamber through the delivery assembly, and whereupon depressing the needle shield toward the housing triggers actuation of the delivery actuation device.

7. The medication mixing and delivery device of claim 1, further including two independent and directionally opposing springs, wherein one spring is a mixing spring that is coupled to the mixing actuation device and upon triggering the mixing actuation device releases energy from the mixing spring that directs the movable body in a first direction, and wherein the other spring is a delivery spring that is coupled to a delivery actuation device and upon triggering the delivery actuation device releases energy that directs the movable body in a second direction.

8. The medication mixing and delivery device of claim 1, further comprising a delivery actuation device coupled to a delivery spring that upon activating the delivery actuation device causes energy from the delivery spring to be released and cause the movable body, which is coupled to a delivery displacement mechanism, to translate in an opposite direction of the movement initially facilitated by the mixing actuation device, thus facilitating displacement of liquid transferred to the second chamber from the first chamber to be displaced through the delivery assembly.

9. The medication mixing and delivery device of claim of 1, wherein the compression chamber contains a gas and the chamber is configured to vent the gas upon activating the mixing actuation device.

10. The medication mixing and delivery device of claim of 1, further comprising a delivery actuation device, and wherein the mixing actuation device and the delivery actuation device are each coupled to a multi-cam system.

11. The medication mixing and delivery device of claim of 10, wherein the multi-cam system is comprised of a three-cam component.

12. A medication mixing and delivery device comprising:
a housing having a first chamber and a second chamber with selectively variable effective volumes;
a first and second displacement component mechanically coupled to a multi-cam system;
a pre-loaded energy source coupled to the multi-cam system;
a first and second trigger coupled to the multi-cam system, wherein triggering the first trigger causes energy to be released from the pre-stored energy and direct the first displacement component to displace a liquid stored in the first chamber through a fluidic channel into the second chamber, and
wherein triggering the second trigger releases additional energy that directs the second displacement component to displace liquid now stored in the second chamber to be displaced and exit through a delivery assembly that is in fluid communication with the second chamber.

13. The medication and delivery device of claim 12, wherein the multi-cam system includes a three-cam component.

14. The medication and delivery device of claim 12, wherein the pre-loaded energy source is comprised of a mixing spring and a delivery spring.

15. The medication and delivery device of claim 14, wherein the delivery spring overcomes and recompresses the mixing spring during an injection step.

16. The medication and delivery device of claim 12, further including a movable body disposed between the first and second chambers, wherein the movable body is coupled to the multi-cam system and is configured to rotate and translate about an axis.

17. The medication and delivery device of claim 16, further comprising a needle shield assembly configured to form part of the second trigger.

18. The medication and delivery device of claim 12, further including a compression chamber separated from the first chamber by a dynamic seal.

19. A medication and delivery device comprising:
a housing having a first chamber and a second chamber with selectively variable effective volumes;
an actuation assembly further comprising:
a first displacement component;
a second displacement component;
a first spring;
a second spring;
wherein a first actuation step of the actuation assembly releases energy stored in the first spring that drives the first displacement component in a first direction, and wherein a second actuation step of the actuation assembly releases energy stored in the second spring that drives the second displacement component in a second direction that is different that the first direction; and
wherein the first actuation causes liquid to transfer from the first chamber to the second chamber, and wherein the second actuation causes fluid to transfer from the second chamber through a delivery assembly.

20. The medication and delivery device of claim 19, wherein the first spring is configured to be in a pre-torqued and compressed state prior to the first actuation.

* * * * *